US007014627B2

(12) United States Patent
Bierman

(10) Patent No.: US 7,014,627 B2
(45) Date of Patent: Mar. 21, 2006

(54) CATHETER SECUREMENT DEVICE

(75) Inventor: Steven F. Bierman, Del Mar, CA (US)

(73) Assignee: Venetec International, Inc., San Diego, CA (US)

( * ) Notice: Subject to any disclaimer, the term of this patent is extended or adjusted under 35 U.S.C. 154(b) by 0 days.

(21) Appl. No.: 10/642,445

(22) Filed: Aug. 15, 2003

(65) Prior Publication Data

US 2004/0102736 A1    May 27, 2004

Related U.S. Application Data

(60) Provisional application No. 60/454,430, filed on Mar. 11, 2003, provisional application No. 60/418,389, filed on Oct. 11, 2002, provisional application No. 60/414,999, filed on Sep. 30, 2002, provisional application No. 60/411,127, filed on Sep. 16, 2002, provisional application No. 60/404,354, filed on Aug. 15, 2002.

(51) Int. Cl.
A61M 5/32    (2006.01)

(52) U.S. Cl. ..................................... 604/174
(58) Field of Classification Search ............... 604/174, 604/180, 177, 178, 179, 533
See application file for complete search history.

(56) References Cited

U.S. PATENT DOCUMENTS

| | | |
|---|---|---|
| 3,046,984 A | 7/1962 | Eby |
| 4,082,094 A | 4/1978 | Dailey |
| 4,129,128 A | 12/1978 | McFarlane |
| D252,822 S | 9/1979 | McFarlane |
| 4,224,937 A | 9/1980 | Gordon |
| 4,250,880 A | 2/1981 | Gordon |
| 4,484,913 A | 11/1984 | Swauger |
| 4,563,177 A | 1/1986 | Kamen |
| 4,711,636 A | 12/1987 | Bierman |
| 4,852,844 A | 8/1989 | Villaveces |
| 4,863,432 A | 9/1989 | Kvalo |
| 5,037,397 A | 8/1991 | Kalt et al. |
| 5,192,273 A | 3/1993 | Bierman |
| 5,192,274 A | 3/1993 | Bierman |
| 5,290,248 A | 3/1994 | Bierman et al. |
| D347,060 S | 5/1994 | Bierman |

(Continued)

FOREIGN PATENT DOCUMENTS

EP    0356683    3/2000

(Continued)

OTHER PUBLICATIONS

U.S. Appl. No. 09/136,271, applicant Steven F. Bierman, filed Aug. 18, 1989.

(Continued)

Primary Examiner—Kevin C. Sirmons
(74) Attorney, Agent, or Firm—Knobbe Martens Olson & Bear LLP

(57) ABSTRACT

A catheter securement device holds a medical article such as a catheter hub or a connector fitting in position upon the body of a patient and at least inhibits longitudinal movement of the medical article. The securement device includes a retainer and at least one anchor pad. The retainer forms a central channel into which at least a portion of the medical article is inserted. The retainer includes at least one abutment that can abut against a contact point or surface on the medical article. The abutment, in conjunction with a second abutment and/or a tapering shape of the central channel, inhibits motion of the medical article in proximal and distal directions through the central channel. For this purpose, the abutment surface(s) can lie either within or outside the channel.

37 Claims, 29 Drawing Sheets

U.S. PATENT DOCUMENTS

| | | |
|---|---|---|
| 5,314,411 A | 5/1994 | Bierman et al. |
| 5,354,282 A | 10/1994 | Bierman |
| 5,413,562 A * | 5/1995 | Swauger .................... 604/179 |
| 5,456,671 A | 10/1995 | Bierman |
| D364,922 S | 12/1995 | Bierman |
| D375,355 S | 11/1996 | Bierman |
| D375,356 S | 11/1996 | Bierman |
| 5,578,013 A | 11/1996 | Bierman |
| D377,831 S | 2/1997 | Bierman |
| 5,693,032 A | 12/1997 | Bierman |
| 5,702,371 A | 12/1997 | Bierman |
| 5,722,959 A | 3/1998 | Bierman |
| 5,800,402 A | 9/1998 | Bierman |
| 5,810,781 A | 9/1998 | Bierman |
| D399,954 S | 10/1998 | Bierman |
| 5,833,667 A | 11/1998 | Bierman |
| 5,855,591 A | 1/1999 | Bierman |
| D425,619 S | 5/2000 | Bierman |
| 6,113,577 A | 9/2000 | Hakky et al. |
| 6,132,398 A | 10/2000 | Bierman |
| 6,213,979 B1 | 4/2001 | Bierman |
| 6,224,571 B1 | 5/2001 | Bierman |
| 6,290,676 B1 | 9/2001 | Bierman |
| 6,361,523 B1 | 3/2002 | Bierman |
| 6,413,240 B1 | 7/2002 | Bierman et al. |
| 6,428,515 B1 | 8/2002 | Bierman et al. |
| 6,447,485 B1 | 9/2002 | Bierman |
| 6,447,486 B1 | 9/2002 | Tollini |
| 6,491,664 B1 | 12/2002 | Bierman |
| 6,500,154 B1 | 12/2002 | Hakky et al. |
| D470,936 S | 2/2003 | Bierman |
| 6,551,285 B1 | 4/2003 | Bierman |
| 6,572,588 B1 | 6/2003 | Bierman et al. |
| 6,582,403 B1 | 6/2003 | Bierman et al. |
| 2002/0068904 A1 | 6/2002 | Bierman et al. |
| 2002/0099360 A1 | 7/2002 | Bierman |
| 2003/0229313 A1 | 12/2003 | Bierman |

FOREIGN PATENT DOCUMENTS

| | | |
|---|---|---|
| WO | WO 94/21319 | 9/1994 |
| WO | WO 97/15337 | 5/1997 |
| WO | WO 99/55409 | 11/1999 |

OTHER PUBLICATIONS

U.S. Appl. No. 10/677,757, applicant Steven F. Bierman, filed Oct. 1, 2003.

U.S. Appl. No. 29/179,916, applicant Steven F. Bierman, filed Apr. 14, 2003.

International Search Report for App. No. PCT/US03/25622, mailed Mar. 10, 2004.

* cited by examiner

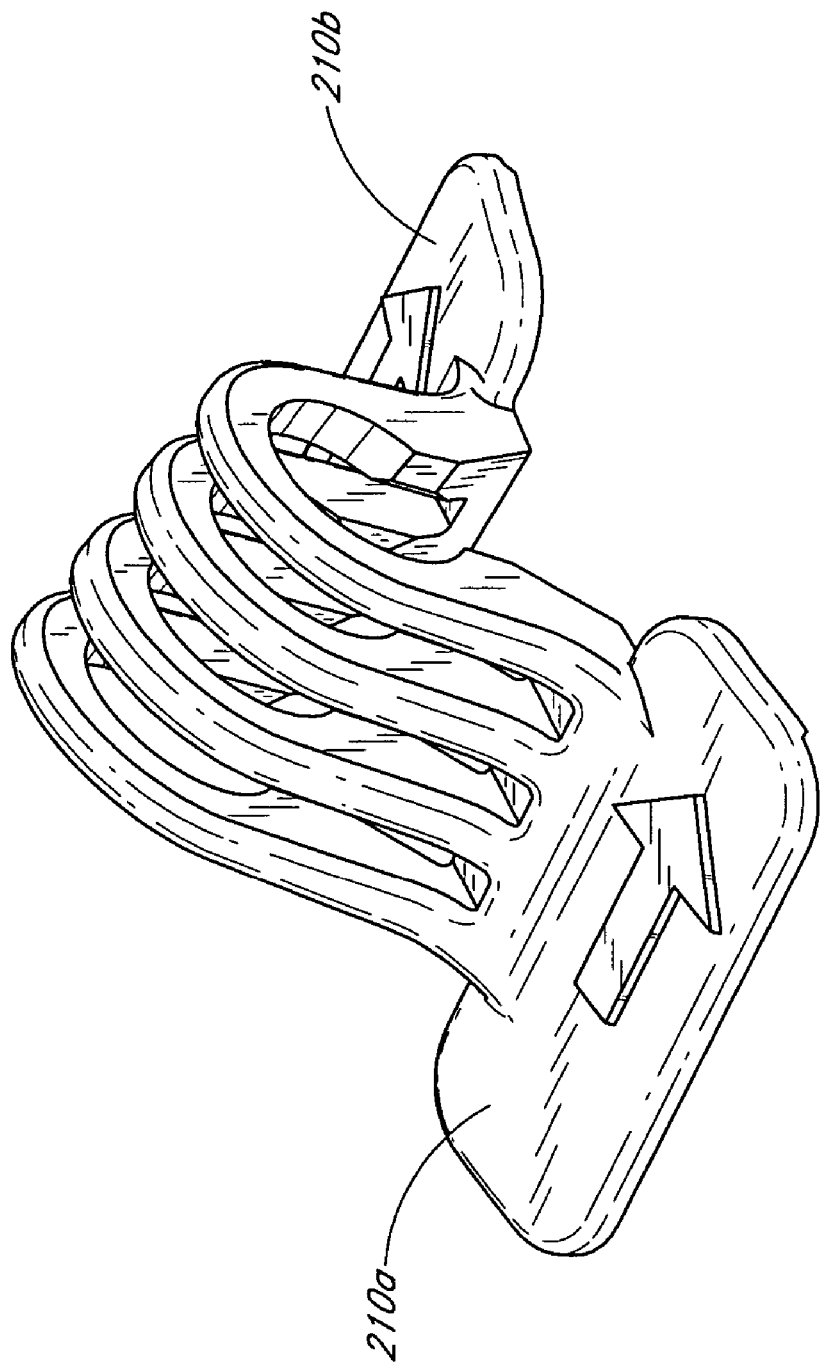

CATHETER SECUREMENT DEVICE

RELATED APPLICATIONS

This application claims priority under 35 U.S.C. § 119(e) to U.S. Provisional Patent Application Ser. Nos. 60/404,354 (filed Aug. 15, 2002), 60/411,127 (filed Sep. 16, 2002), 60/414,999 (filed Sep. 30, 2002), 60/418,389 (filed Oct. 11, 2002), and 60/454,430 (filed Mar. 11, 2003), all of which are hereby expressly incorporated by reference in their entireties.

BACKGROUND OF THE INVENTION

1. Field of the Invention

This invention relates to a securement system used to attach a medical line to a patient.

2. Description of the Related Art

It is common in the treatment of patients to utilize catheters to introduce fluids and medications directly into the patient or to withdraw fluids from the patient. Often, it becomes desirable to maintain such catheterization over an extended period of time during the treatment of a patient. In order to keep the catheter or other medical line properly positioned for the duration of treatment, the catheter or medical line can be secured to the patient in a variety of ways. Most commonly, this involves taping the catheter or medical line to the patient.

Securing a catheter with tape upon the patient traditionally has certain drawbacks. The use of tape at the insertion site can retain dirt or other contaminant particles, potentially leading to infection of the patient. Tape also fails to limit catheter motion and, therefore, contributes to motion related complications like phlebitis, infiltration and catheter migration. Additionally, removal of taped dressings can itself cause undesired motion of the catheter upon the patient.

Taped dressings also require periodic changes. The frequent, often daily, removal and reapplication of adhesive tape to the skin of the patient can excoriate the skin in the area around the dressing. Such repeated applications of tape over the catheter or medical line can additionally lead to the build up of adhesive residue on the outer surface of the catheter or medical line. This residue can result in contaminants adhering to the catheter itself, increasing the likelihood of infection of the insertion site. This residue can also make the catheter or medical line stickier and more difficult to handle for healthcare providers.

SUMMARY OF THE INVENTION

The systems and methods of the present invention have several features, no single one of which is solely responsible for its desirable attributes. Without limiting the scope of this invention as expressed by the claims which follow, its more prominent features will now be discussed briefly. After considering this discussion, and particularly after reading the section entitled "Detailed Description of the Preferred Embodiments" one will understand how the features of this invention provide several advantages over traditional catheter securement systems.

One aspect of the present invention is a medical line securement system that comprises a medical article, at least one anchor pad including a lower adhesive surface configured to attach to an epidermal layer of a patient, and a retainer. The retainer comprising a body member having a channel formed therethrough about a channel axis, the channel being configured to retain at least a portion of the medical article and having a longitudinal access opening disposed on an underside of the body member to allow at least ingress of the portion of the medical article into the channel. The retainer further comprising at least one abutment extending generally normal to the channel axis and configured to inhibit longitudinal movement of the medical article and at least one support disposed on the underside of the retainer and to a side of the access opening opposite the channel axis, the support attached to the anchor pad.

Another aspect of the invention is a retainer configured for use with a medical article. The retainer comprises a body member which comprising a channel formed through the body member, the channel being configured to retain at least a portion of the medical article and having a longitudinal access opening disposed on an underside of the body member to allow at least ingress of the medical article into the channel. The body member further comprising at least one abutment extending generally normal to an axis of the inverted channel and configured to inhibit longitudinal movement of the medical article and at least one support disposed on the underside of the retainer and to a side of the access opening opposite the channel axis.

Another aspect of the invention is a retainer that is configured for use with a medical article. The retainer comprises a body member which comprises a channel formed through the body member, the channel being configured to retain at least a portion of the medical article and having a longitudinal access opening disposed on an underside of the body member to allow ingress of the portion of the medical article into the channel. The body member further comprising at least one abutment extending generally normal to an axis of the channel and configured to inhibit longitudinal movement of the medical article and means for holding the medical article away from a patient's skin.

Yet another aspect of the invention is a retainer that is configured for use with a medical article that comprises a radially extending member. The retainer comprises a body member having proximal and distal ends and further comprises a channel formed through the body member, the channel being configured to retain at least a portion of the medical article and having a longitudinal access opening disposed on an underside of the body member to allow at least ingress of the medical article into the channel. The body member further comprises at least one slot disposed between the proximal and distal ends of the body member and configured to receive the radially extending member and a stop member extending into a portion of the at least one slot such that when the medical article is inserted into the channel and rotated in a first direction around the axis of the channel, the radially extending member slides within the slot until the radially extending member contacts the stop member.

Another aspect of the invention is a method of securing a medical article to a patient. The method comprises providing a medical article, providing a retainer having a channel formed therethrough, the channel being configured to receive and retain the medical article, and at least one abutment extending generally normal to the channel, and positioning the retainer over the medical article. The method further comprises pressing the medical article into the channel through an opening formed on the underside of the retainer, abutting the medical article against the abutment to inhibit longitudinal motion of the medical article relative to the retainer in at least one direction, and after pressing the article into the body member, adhering the retainer relative to a patient's skin.

Still another aspect of the invention is a medical line securement system that comprises a medical article having a connector and a retainer. The retainer comprises a body member having a channel formed therethrough, the channel being configured to retain at least a portion of the medical article and having a longitudinal access opening disposed on an underside of the body member to allow ingress of the portion of the medical article into the channel and at least one abutment extending generally normal to an axis of the channel and configured to inhibit longitudinal movement of the medical article. The retainer further comprises at least one support surface disposed on the underside of the retainer and to a side of the access opening opposite the channel axis and wherein an overall length of the retainer is less than a length of the medical article.

A further aspect of the invention is a retainer configured for use with a medical article. The retained comprises a body member which comprises a channel formed therethrough, the channel being configured to retain a portion of the medical article and having a longitudinal access opening disposed on an underside of the body member to allow ingress of the medical article into the channel. The body member further comprising at least one abutment extending generally normal to an axis of the channel and configured to inhibit longitudinal movement of the medical article and at least one support disposed on the underside of the retainer and to a side of the access opening opposite the channel axis, wherein a distance between the at least one support and the axis of the channel prevents contact between the medical article and a patient's skin when the retainer is placed upon the patient's skin.

A still further aspect of the invention is a retainer configured for use with a medical article. The retainer comprises a body member which comprises a channel formed therethrough, the channel being configured to retain the medical article and having a longitudinal access opening disposed on an underside of the body member to allow ingress of the medical article. The body member further comprises at least one abutment extending generally normal to an axis of the channel and configured to inhibit longitudinal movement of the medical article and at least one support disposed on the underside of the retainer and to one side of the access opening opposite the channel axis, wherein the support surface provides a mounting surface for attachment of the retainer to a patient's skin, and wherein the mounting surface is angled relative to the longitudinal access opening to define an incident angle between the axis of the channel and the patient's skin.

BRIEF DESCRIPTION OF THE DRAWINGS

FIG. 27B is a front perspective view of the retainer of FIG. 27A.

DETAILED DESCRIPTION OF THE PREFERRED EMBODIMENTS

The following description and the accompanying figures, which describe and show the preferred embodiments, are made to demonstrate several possible configurations that a securement system can take to include various aspects and features the invention. The illustrated embodiments are shown in use with either one or both of an illustrative example of a catheter hub and an illustrative example of a connector fitting with a spin nut for connection to the catheter hub. The illustration of the securement device in this context is not intended to limit the disclosed aspects and features of the invention to the specified embodiments or to usage only with the illustrated connector or hub. Those of skill in the art will recognize that the disclosed aspects and features of the invention are not limited to any particular embodiment of a securement system, and securement systems, which include one or more of the inventive aspects and features herein described, can be designed for use with a variety of medical articles.

Figure 1:
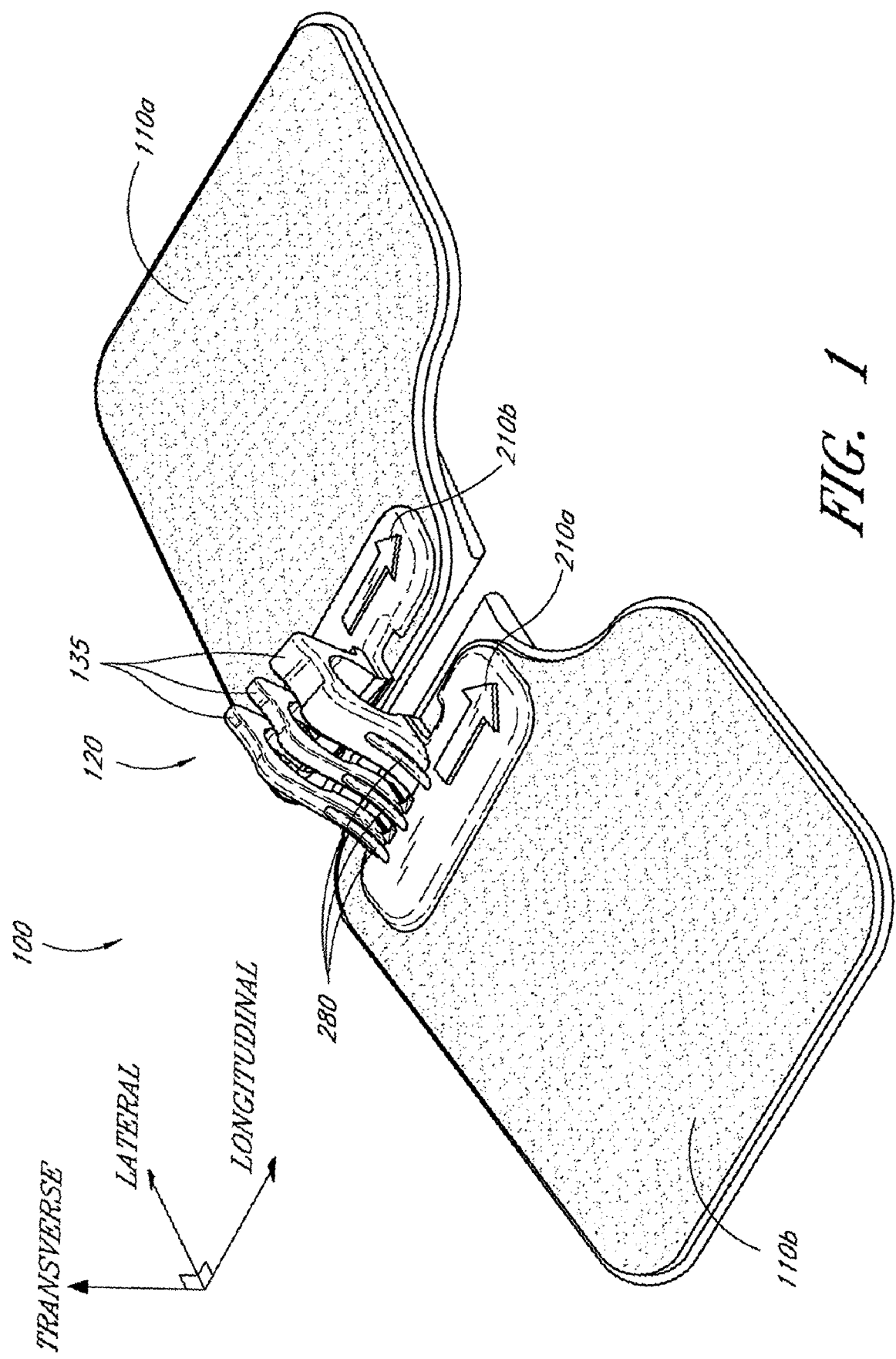
FIG. 1 is a perspective view of the securement device configured in accordance with a preferred embodiment of the present invention.

To assist in the description of these components of the securement system, the following coordinate terms are used (see FIG. 1). A "longitudinal axis" is generally parallel to a portion of the catheter hub, the connector fitting or other medical article retained by the securement system, as well as parallel to the axis of a channel of the retainer, through which the medical article extends. A "lateral axis" is normal to the longitudinal axis. A "transverse axis" extends normal to both the longitudinal and lateral axes. In addition, as used herein, "the longitudinal direction" refers to a direction substantially parallel to the longitudinal axis; "the lateral direction" refers to a direction substantially parallel to the lateral axis; and "the transverse direction" refers to a direction substantially parallel to the transverse axis. The term "axial" as used herein refers to the axis of the channel or connector fitting, and therefore is substantially synonymous with the term "longitudinal" as used herein. Also, the terms "proximal" and "distal", which are used to describe the present securement system, are used consistently with the description of the exemplary applications (i.e., the illustrative examples of the use applications). Thus, proximal and distal are used in reference to the center of the patient's body. The terms "upper," "lower," "top," "bottom," "underside," "upperside" and the like, which also are used to describe the present securement system, are used in reference to the illustrated orientation of the embodiment. For example, the term "upperside" is used to describe the portion of the retainer that is located above a lateral axis that passes through the axis of the channel. The term "underside" is used to describe the portion of the retainer that is located below a lateral axis that passes through the axis of the channel. Brief introductions to some of the features, which are common to the described embodiments of the securement systems, are now described. In the illustrated embodiment, the arrows on the securement device point in the direction toward the insertion site (i.e., in the proximal direction).

The preferred embodiments of the present invention advantageously provide a medical line securement system for securing a medical article to a patient. The medical article preferably has an elongated body. The elongated body cooperates with a retainer to arrest movement of the medical article in longitudinal, lateral, and transverse directions when placed within the retainer.

In each of the embodiments described below, the retainer has a body member which includes an inverted channel formed therethrough. The inverted channel has a longitudinal access opening located on an underside of the retainer to allow ingress or egress of the medical article. The medical article is installed or removed from the underside of the retainer via this access opening. Such an arrangement allows the medical provider to align at least a portion of the medical article with the retainer prior to fixing the retainer to the patient's skin. In this way, the inverted channel retains a portion of the medical article.

The retainer includes at least one abutment (preferably an abutment surface) that cooperates with at least one contact point or surface on the medical article. The one or more abutments of the retainer extend generally normal to the axis of the channel and can be, for example, but without limitation a surface, a wall of a slot, a ridge, a protuberance, or like structures. The abutment cooperates with the one or more contact points or surfaces of the medical article to inhibit longitudinal movement of the medical article through the channel. For example, the abutment could be a surface on the distal end of the retainer that acts against at least a portion of a radially extending member or spin nut of the medical article. In this way, the medical article will be limited in it proximal movement (i.e., movement toward the patient) once the radially extending member contacts or abuts against the distal end of the retainer.

The retainer of each embodiment described below further includes at least one support that is preferably disposed on the underside of the retainer at a position lower than the access opening. With this construction, the retainer holds the retained portion of medical article away from the patient's skin, when the retained portion is positioned within the retainer channel, to avoid chaffing or excoriating the skin. The support in each of the illustrated embodiments includes left and right mounting wings that are integral with the body member and are attached to left and right anchor pads. The lower surfaces of the left and right anchor pads attach to the patient's skin.

The retainer and anchor pad(s) also can have other constructions in order to inhibit contact between the skin and the retainer, as well as between the skin and the retained portion of the medical article. For example, the anchor pads can be thicker, in which case the mounting wings can be located higher on the retainer body.

To facilitate a complete understanding of the embodiment, the remainder of the detailed description describes the securement system with reference to the figures, wherein like elements among the embodiments are referenced with like numerals throughout the following description.

Figure 2:
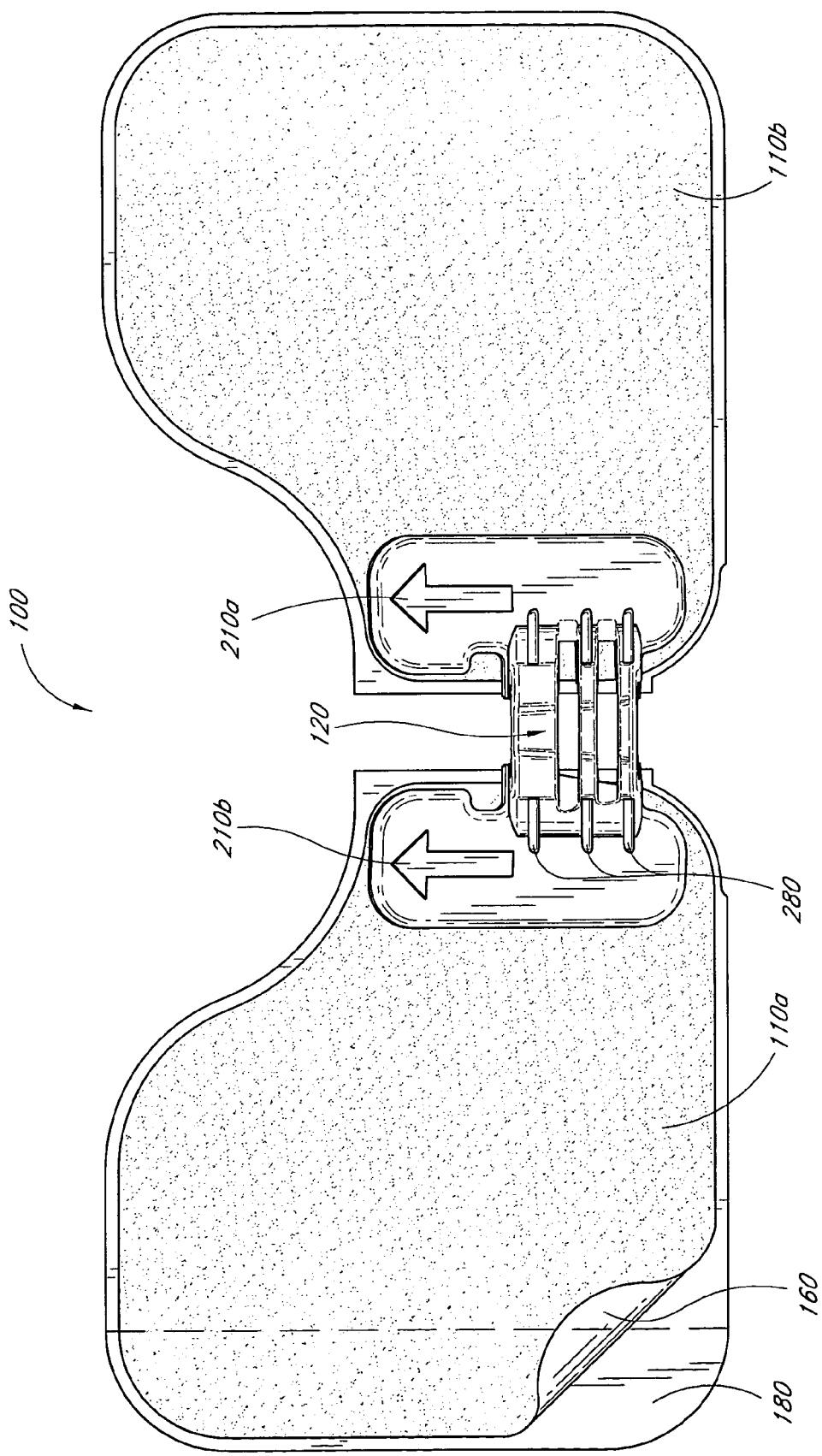
FIG. 2 is a top plan view of the securement device of FIG. 1 that includes a retainer and anchor pads.

FIG. 1 is a perspective view of a securement device 100 configured in accordance with an embodiment of the present invention and FIG. 2 is a top plan view of the securement device 100 of FIG. 1. As shown in FIGS. 1 and 2, the illustrated securement device 100 comprises three main components: two anchor pads 110(a), 110(b) and a retainer 120. The illustrated retainer 120 includes a left footing/mounting wing 210(a) and right footing/mounting wing 210(b). Each mounting wing is disposed upon the respective one of the anchor pads 110(a), 110(b). The mounting wings 210(a), 210(b) extend in a lateral direction away from a center of the retainer 120.

As noted above, the securement device 100 can form a component of a catheterization or securement system that also includes one or more medical articles, such as connector fittings, catheters, hubs, catheter adaptors, fluid supply lines, or other articles suitable for securement via the anchor pads and retainer. An opening in the retainer 120 is aligned with the medical article. The medical article is inserted between the anchor pads 110(a), 110(b), through the opening, and into the retainer 120. The anchor pads 110(a), 110(b) are then secured to the skin of the patient, generally by an adhesive disposed upon the bottom surface of the pads. In this way, the retainer 120 secures the medical article to the patient. Thus, the retainer at least restricts, if not prevents, lateral and transverse movement of the retained section of the medical article. Additional features of the securement device 100 can restrict, if not prevent, longitudinal and rotational movement of the retained section of the medical article. The embodiment illustrated is preferably for use with a catheter adapter or hub, as described with reference to FIGS. 15A and 15B. The embodiments of the anchor pad and the retainer are described in more detail below.

Anchor Pad

Figure 3:
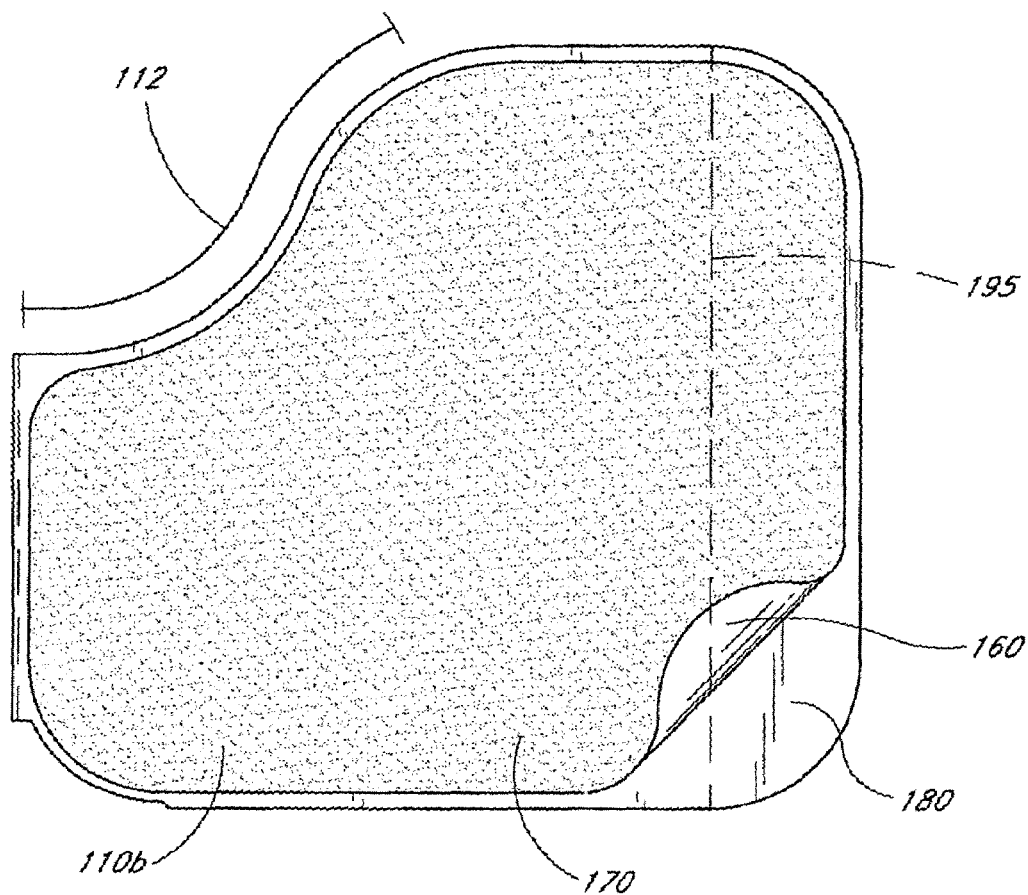
FIG. 3 is a top plan view of a right anchor pad of FIG. 2.
Figure 4:
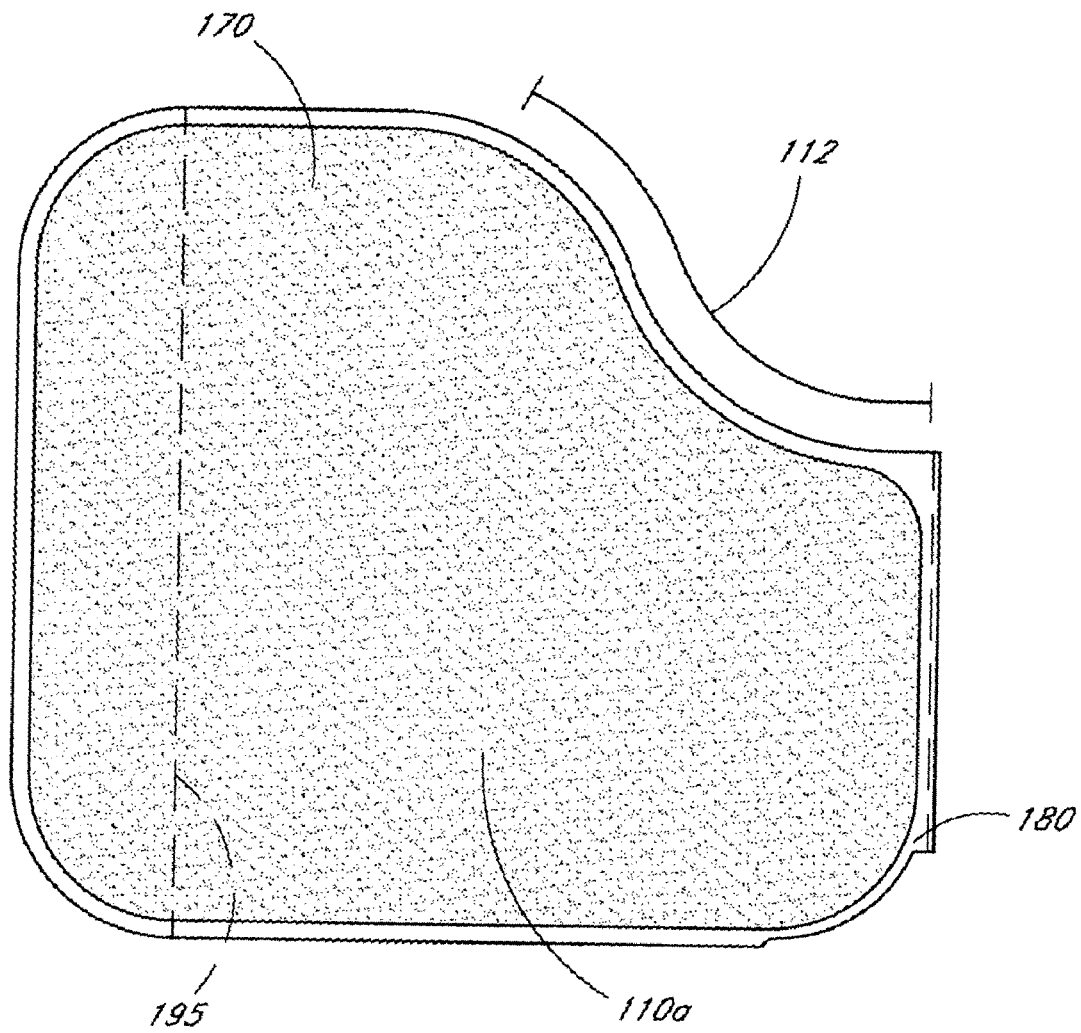
FIG. 4 is a top plan view of a left anchor pad of FIG. 2.

FIGS. 3 and 4 illustrate the anchor pads 110(b), 110(a), respectively, apart from the rest of the securement device 110 shown in FIG. 2. The general structure of each anchor pads 110(a), 110(b) comprises a generally rectangular shape with a scalloped region 112 located at a corner of each anchor pad. The scalloped configuration eases the process of aligning the securement device 100 with a catheter insertion site in the patient's skin. Although only a single shape of the anchor pad is illustrated in FIGS. 3 and 4, those of skill in the art will recognize that a variety of shapes can be used.

Each anchor pad 110 desirably comprises a laminate structure with an upper plastic, paper or foam layer (e.g., closed-cell polyethylene foam) and a lower adhesive layer. The lower adhesive layer constitutes a lower surface 160 of the anchor pad. The lower surface 160 desirably is a medical-grade adhesive and can be either diaphoretic or nondiaphoretic, depending upon the particular application. Such foam with an adhesive layer is available commercially from Avery Dennison of Painsville, Ohio. While not illustrated, the anchor pads 110(a), 110(b) can include suture holes in addition to the adhesive layer to further secure the anchor pad to the patient's skin.

In other variations, a hydrocolloid adhesive or zinc oxide-based adhesive can advantageously be used upon the anchor pads 110(a), 110(b) for attaching the anchor pads to the skin of the patient. The hydrocolloid or zinc oxide-based adhesive can be used either alone or in combination with another medical grade adhesive (e.g., in combination with the adhesive available from Avery Dennison). Hydrocolloid and zinc oxide-based adhesives have less of a tendency to excoriate the skin of a patient when removed. This can be particularly important for patients whose skin is more sensitive or fragile, such as neonates and those with a collagen deficiency or other skin related condition.

In another variation, each anchor pad 110(a), 110(b) comprises a laminate structure with an upper woven layer and a lower adhesive layer. The upper layer can be polyester or other suitable polymer or textile materials. One particular suitable material is a woven polyester available commercially under the name "Tricot" from Tyco. The lower adhesive layer constitutes the lower surface 160 of the anchor pad. The lower surface desirably is a medical-grade adhesive and can be either diaphoretic or nondiaphoretic, depending upon the particular application.

A surface of the upper foam layer constitutes an upper surface 170 of the anchor pads 110(a), 110(b). The upper surface 170 can be roughened by corona-treating the foam with a low electric charge. The roughened or porous upper surface can improve the quality of the adhesive joint (which is described below) between the mounting wings 210 and the anchor pads 110. In a further variation, the flexible anchor pad can comprise an upper paper or other woven or nonwoven cloth or plastic layer in lieu of a roughened upper foam surface.

The anchor pads 110(a), 110(b) preferably are arranged with respect to the retainer 120 such that the tip of the medical article does not extend beyond the front edge of the mounting wings 210 when the medical article is properly inserted within the retainer 120. The healthcare provider can be instructed to generally align the medical article tip with the front edges of the anchor pads 110(a), 110(b) before inserting the medical article into the retainer 120.

As illustrated in FIG. 3, a removable paper or plastic release liner 180 desirably covers the adhesive lower surface 160 before use. The liner 180 preferably resists tearing and desirably is divided into a plurality of pieces to ease attachment of the pad to a patient's skin.

The liner 180 comprises a folded over portion to define a pull tab 190 (see FIG. 1). The pull tab can be utilized to remove the paper or plastic release liner 180 from their adhesive lower surface 160 before use. A healthcare provider uses the pull tab 190 by grasping and pulling on it so that the liner 180 is separated from the lower surface 160. The pull tab 190 overcomes any requirement that the healthcare provider pick at a corner edge or other segment of the liner in order to separate the liner from the adhesive layer.

The pull tab 190 of course can be designed in a variety of configurations. For example, the pull tab 190 can be located along a center line of the anchor pad 110; or alternatively, the pull tab can be located along any line of the anchor pad 110 in order to ease the application of the anchor pad onto the patient's skin at a specific site. For example, an area of a patient's skin with an abrupt bend, such as at a joint, can require that the pull tab 190 be aligned toward one of the lateral ends of the anchor pad 110 rather than along the center line. In the embodiment illustrated in FIGS. 3 and 4, the pull tab 190 extends from a bottom surface of the anchor pads 110(a), 110(b) and along an outer line 195.

The fold that forms the pull tab 190 preferably occurs laterally beyond the inner (medial) edge on each anchor pad 110(a), 110(b), as best seen in FIG. 2, rather than at the inner edge of the anchor pad 110(a), 110(b). Thus, the spacing between the folds of the release liners 180 is less than the spacing between the inner edges of the anchor pads 110(a), 110(b). The projection of the release linear beyond the anchor pad inner edge provides an area onto which any adhesive, which is used to attach the retainer to the anchor pad, can run while lessening the occurrence of such adhesive contacting the fold. Cracks often occur at the fold and presence of adhesive in such cracks can create delimitation of the release liner and incomplete removal of the release linear when peeled away from the corresponding anchor pad 110(*a*), 110(*b*).

Additionally, the distal side of each release linear is cut to increase a "view window" through which a healthcare provider can see when aligning the retainer over the medical article (e.g., the catheter hub and/or the connector fitting). Preferably, the resulting relief originates from the inner edge of the release linear generally at a right angle thereto and then transitions into a shape that generally matches the shape of the adjacent region of corresponding anchor pad 110(*a*), 10(*b*). The initial right-angle cut of this relief reduces instances of the release linear ripping when properly pulled in the lateral direction away from the retainer 120.

Retainer

Figure 5:
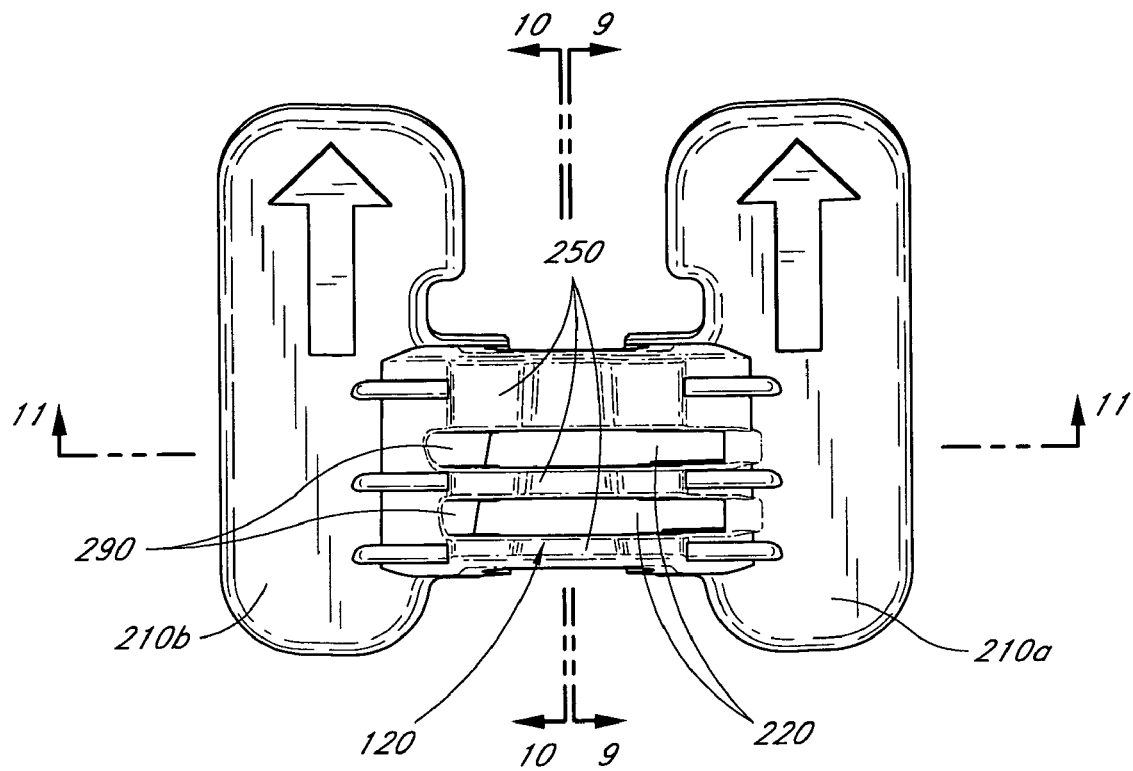
FIG. 5 is a top plan view of the retainer of FIG. 2.
Figure 6:
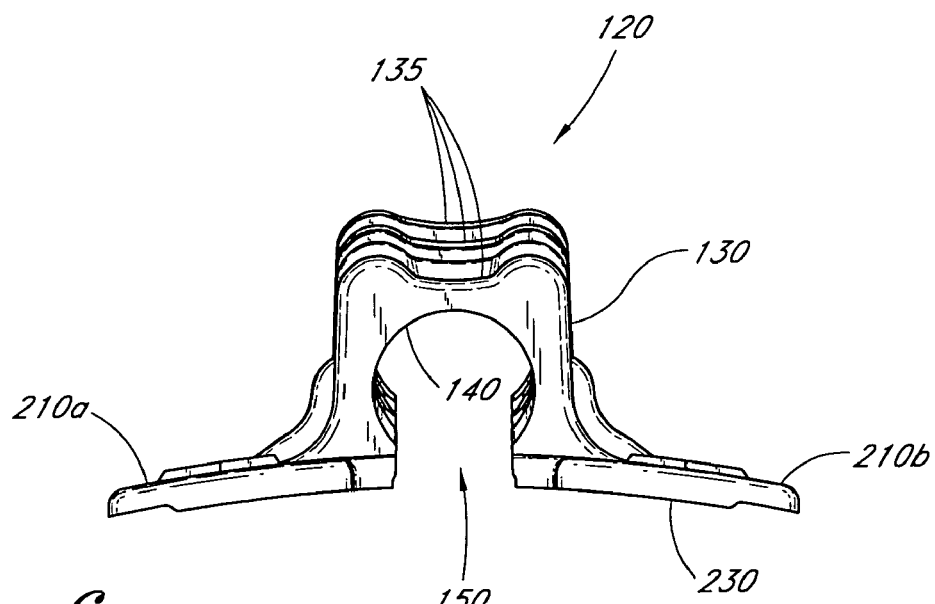
FIG. 6 is a front side view of the retainer of FIG. 5.
Figure 7:
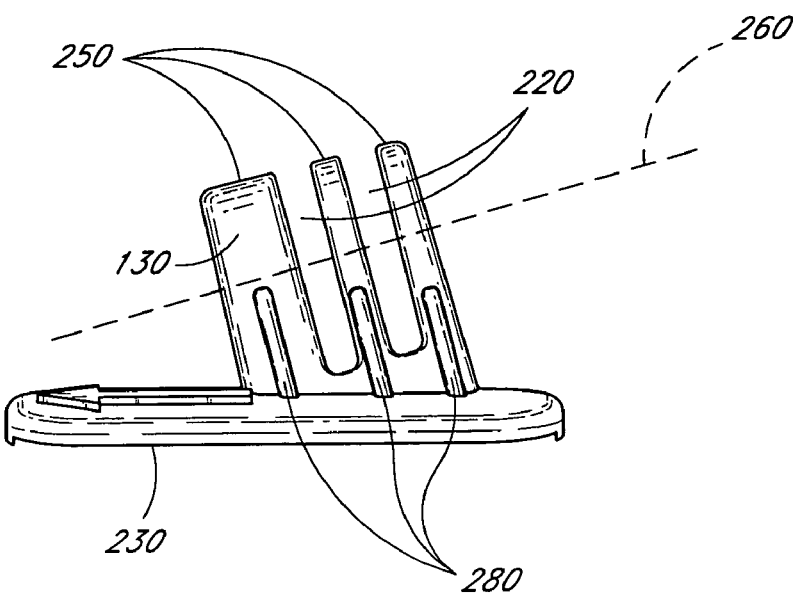
FIG. 7 is a side view of the retainer of FIG. 5.
Figure 8:
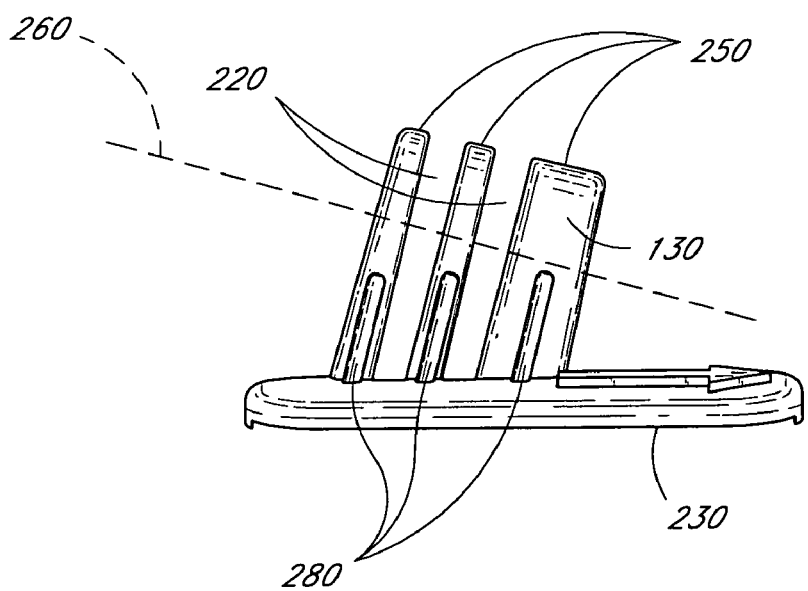
FIG. 8 is a side view of the retainer of FIG. 5.

An embodiment of the retainer 120 is described with reference to FIGS. 5–13. FIG. 5 is a top plan view of the retainer 120 which limits rotation of an installed catheter hub as well as arrests movement of the catheter hub in the longitudinal, lateral and transverse directions. FIG. 6 is a front side view of the retainer 120 from FIG. 5 and illustrates a body member 130 and footings/side mounting wings 210(*a*), 210(*b*) that extend in a lateral direction from either side of the body member. As shown in FIGS. 7 and 8, the body member 130 is elongated in the longitudinal direction and comprises a generally parallelepiped shape. It is advantageous for the longitudinal dimension of the body member 130 to be sufficiently long to provide stability to the retained portion of the medical article along its length. In this way, the longitudinal length of the retained portion is sufficient to inhibit the rocking of the medical article within the retainer 120. Also, the lateral dimension of the body member 130 of the retainer desirably allows the healthcare provider to easily and naturally grip the body member.

With reference to FIG. 6, the inner side of the body member 130 faces towards the patient's skin when in use and preferably defines an inverted central channel 140. The inverted channel 140 extends on the underside of the body member 130 in a longitudinal direction for receiving a section of the catheter hub in the illustrated embodiment.

Figure 14A:
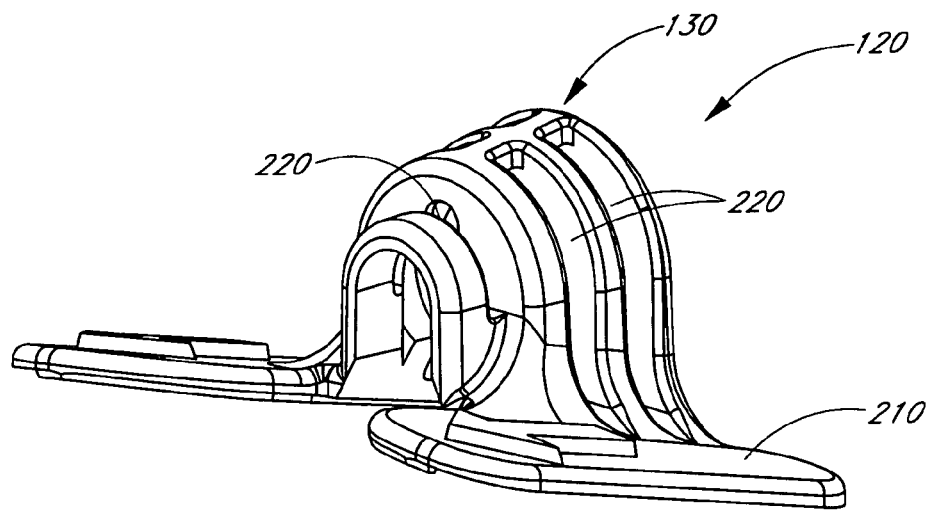
FIG. 14A is a perspective view of a retainer configured in accordance with another preferred embodiment in which the inverted channel has a tapering distal section, a generally constant size proximal section and an abutment surface facing distally between the proximal and distal sections of the channel.
Figure 14B:
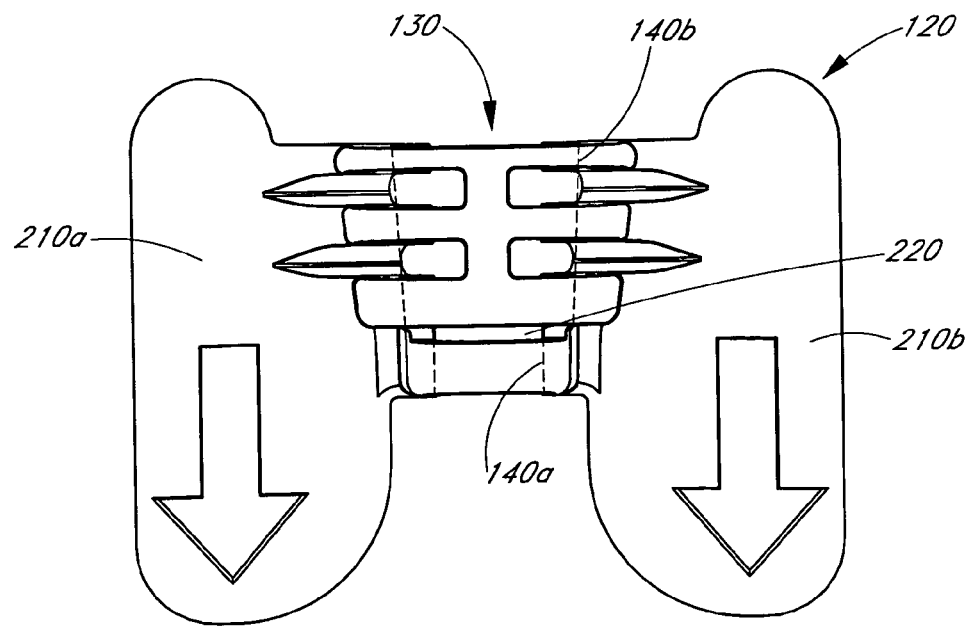
FIG. 14B is a top plan view of the retainer of FIG. 14B and illustrates proximal and distal sections of the channel.

The channel 140 is capable of receiving a portion or length of the medical article and is generally configured to house, to preferably grip, and to secure this portion of the medical article. In the illustrated embodiment (see FIGS. 5 through 8), the central channel 140 has a generally semicircular cross-sectional shape. An inner surface contour of the central channel 140 preferably is selected depending on the geometry of the portion of the medical article to be retained. For example, in a retainer 120 that is configured to retain a portion of a medical article that has a constant outer diameter, the central channel 140 preferably has a constant radius along its length. In contrast, in a retainer 120 configured to retain a portion of a medical article that has a tapering outer surface, the central channel 140 preferably has a tapering inner surface and a radius that varies along the channel length. Additional embodiments of the central channel 140 of the retainer can comprise a plurality of different radii and/or tapering regions. For example, as illustrated in FIGS. 14A and 14B, the channel 140 can have two sections: a first proximal section 140(*a*) have a generally uniform cross-sectional size along its length while a second distal section 140(*b*)has a tapering shape along its length. An abutment wall forms a transition between these two sections of the channel. These sections 140(*a*), 140(*b*) of the channel 140 can also both be tapered or straight (i.e., have a generally uniform radius along the length of the section) or the distal section can be straight and the proximal section can be tapered. In this way, the size and shape of the central channel 140 can be chosen to match or to approximate the size and shape of the medical article or portion thereof, e.g., the catheter hub, to be retained. By matching the inner surface contour of the central channel 140 to the outer surface of the secured portion of a medical article, a more effective securement may be achieved. In addition or in the alternative, effective securement can also be achieved by the engagement of one or more abutment surface of the retainer with one or more contact surfaces on the medical article. Each abutment surface can cooperate with a contact surface on the medical article to inhibit movement of the medical article relative to the retainer. Exemplary abutment surfaces and contact surfaces are described below with reference to FIGS. 16–18.

Although the central channel 140 can be formed in various shapes depending upon the desired application (e.g., depending upon a shape of the retained portion of the medical article for which the retainer is designed to be used), the central channel 140 desirably has a sufficient length in the longitudinal direction to stabilize the connector fitting, catheter hub, or other medical article, rather than act as a fulcrum for the fitting, as mentioned above. That is, the retainer 120 receives a sufficient length of the catheter hub to inhibit movement of the hub in the lateral, longitudinal and transverse direction (i.e., to inhibit yaw, pitch and axial movement of the article).

Figure 12:
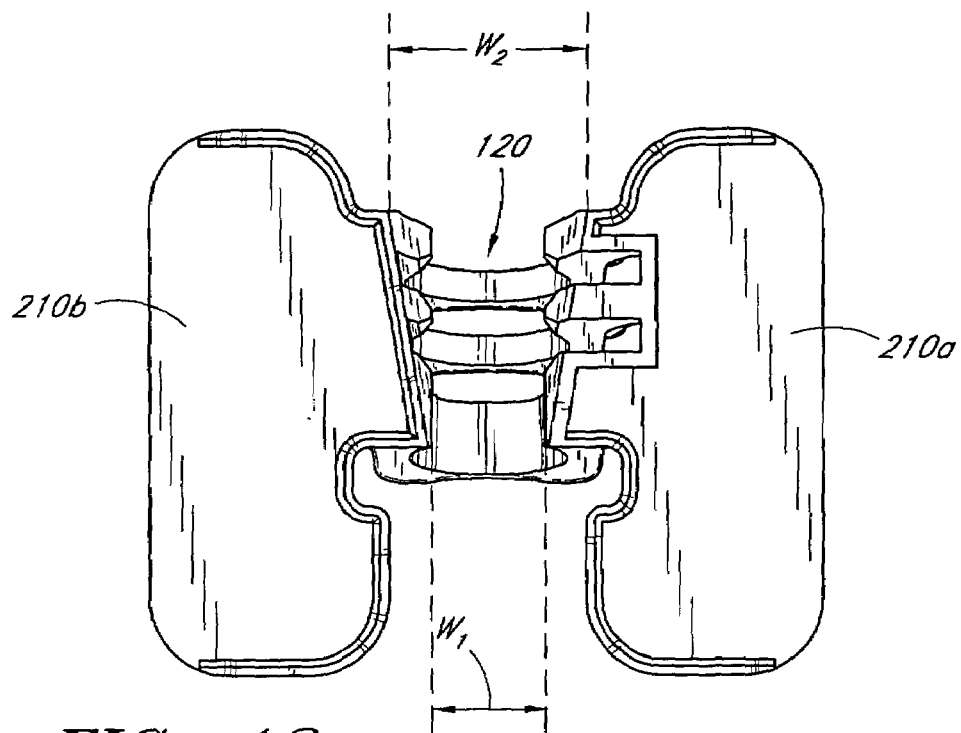
FIG. 12 is a bottom plan view of the retainer of FIG. 5 and illustrates that the distance between the side mounting wings varies in the region of the retainer.

As shown most clearly in FIGS. 6 and 12, the lower side of the retainer 120 includes an access or lower opening 150. In some embodiments, the lower opening 150 has generally tapering sides along the longitudinal axis to match generally the shape of the medical article. In other embodiments, the lower opening 150 has generally parallel sides while the channel 140 is tapered to match generally the shape of the medical article. The lower opening 150 may include contouring (e.g., chamfers) along its periphery in order to guide the medical article into the central channel 140 when inserting the medical article into the retainer 120.

The illustrated retainer 120 further comprises at least one retention surface 165(*a*), 165(*b*) disposed on a lower side of the inverted channel 140. The retention surface holds at least a portion of the retained medical article within the channel 140 and hence away from the patient's skin. This support can be provided by, for example, an adhesive, a region of the inverted channel which provides a degree of snap-fit with the retained medical article, two or more regions of the inverted channel which provide a degree of snap-fit with the retained medical article, or a combination of the adhesive and a region of snap-fit. The adhesive can be located on one or more surfaces of the retainer 120 that contact the medical article. For example, the adhesive could be located on the surface of the inverted channel or on an abutment. Accordingly, any one or more of these elements and structures can provide means for preventing contact between the medical article and a patient's skin.

Figure 9:
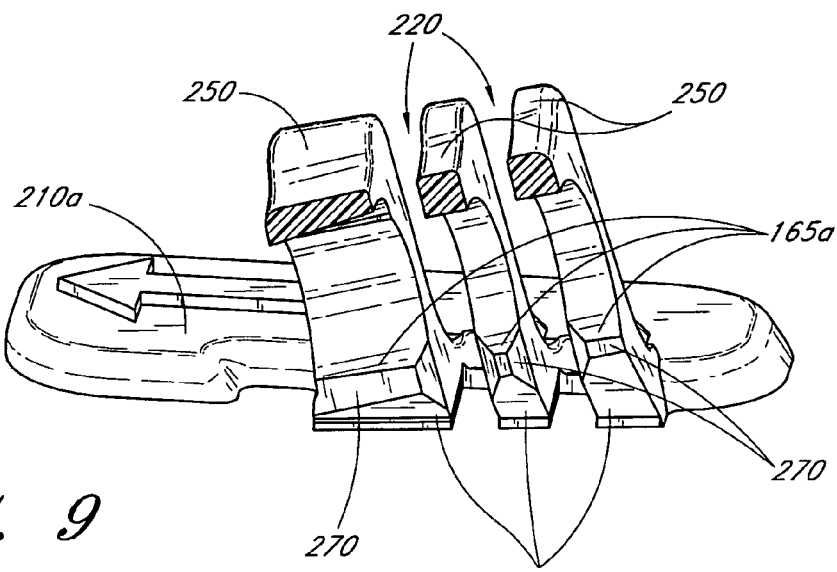
FIG. 9 is a cross-section view of the retainer taken along section 9—9 of FIG. 5.
Figure 10:
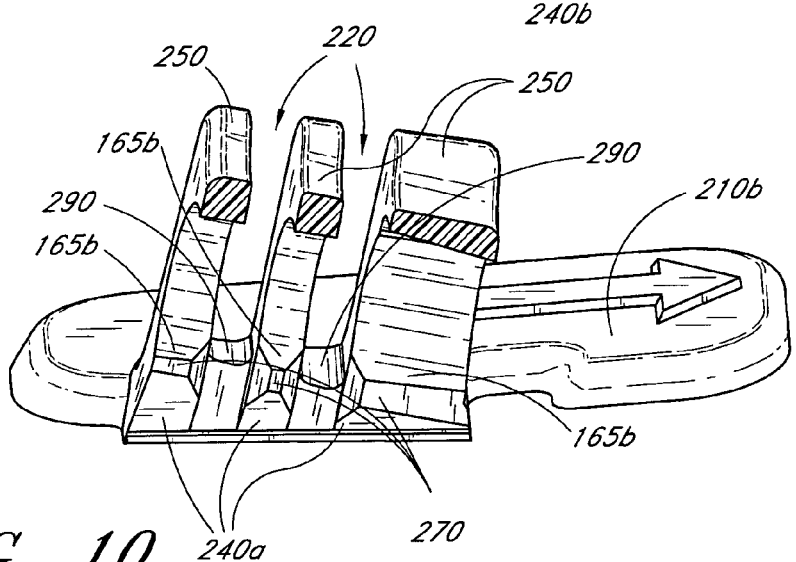
FIG. 10 is a cross-section view of the retainer taken along section 10—10 of FIG. 5.
Figure 11:
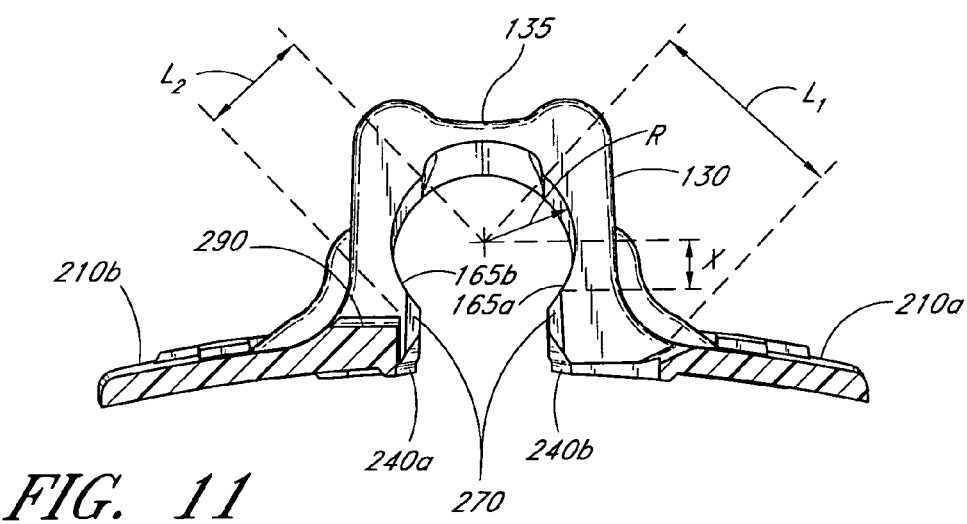
FIG. 11 is a cross-section view of the retainer taken along section 11—11 of FIG. 5 and illustrates an optional wall or stop member in the preferred embodiment that extends into the path of the one or more slots in the region of the mounting wing 210(b).

As shown most clearly in FIGS. 9 through 11, the present embodiment of the retainer 120 includes multiple pairs of retention surfaces 165(*a*), 165(*b*). The corresponding retention surfaces 165(*a*), 165(*b*) of each pair lie on opposite sides of the access opening 150 from each other. In this embodiment, the retention surface 165(*a*) is a portion of the surface that defines the central channel 140 and is located on the lower side of the central channel 140. The retention surface 165(*a*) is located to one side of the central axis. The other retention surface 165(*b*) is a portion of the surface that defines the central channel 140 and is located on the lower side of the central channel 140. The retention surface 165(b) is further located to the side of the central axis that is opposite to the retention surface 165(a). Once the medical article is placed in the central channel 140, the retention surfaces 165(a), 165 (b) each hold a portion of the retained section of the article within the channel 140. While multiple retention surfaces are illustrated in FIGS. 9 through 11, either retention surface 165(a), (b) can be individually employed in variations of the present retainer and still support the medical article within the channel 140.

As shown most clearly in FIG. 11, the retention surfaces 165(a), 165(b) are both located generally at a distance X measured in a transverse direction from the axis of the central channel 140. Distance X preferably is less than radius R when measured at the same location along the central channel 140.

Pressure can be provided by the retention surfaces 165 which holds the medical article within the retainer 120 in the illustrated embodiment. The retention surfaces 165 provide a degree of snap fit between the retainer 120 and the medical article. The degree of snap-fit can be increased by extending the overall surface of the central channel 140 through an arc of greater than 180°. As shown most clearly in FIG. 6, in one embodiment the arc extends for more than 180 degrees in order to more firmly support the retained portion of the medical article. In the illustrated embodiment, the walls of the central channel 140 extend through an arc of approximately 270°. The length of such an arc provides a snap-fit securement between the central channel 140 on the body member 130 and the secured portion of the medical article. In this way, the medical article can be placed in position prior to attaching the securement device 100 to the patient without concern that the medical article will shift while the healthcare provider is attaching the device 100 to the patient. Additionally, the releasable engagement provided by snap-fit connection also permits the retained portion of the medical article to be readily released from retainer 120.

In the illustrated embodiment, as best seen in FIG. 11, chamfered surfaces 240(a) are formed on the underside of the retainer body 130 along one of the lower edges of the access opening 150. A second set of chamfered surfaces 240(b) are formed on the underside of the retainer body 130 along the other lower edge of the access opening 150. The portions of the retainer body 130 between these chamfered surfaces 240 and the retention surfaces 165 form hips 270. In other words, the hips 270 are the portion of the body 130 that is defined by a lower side of the central channel 140 (either the retention surfaces 165(a) on one side of the central axis or the retention surfaces 165(b) on the other side of the central axis), the chamfered surfaces 240, and the sides of the narrow lower opening 150. In one embodiment, the chamfered surfaces 240(a) on one side of the central axis are oblique to the chamber surfaces 240(b) on the other side of the central axis and help guide the medical article into the lower opening 150 and the central channel 140.

The retainer 120 can include a generally rigid structure (at least in comparison to foam or tape) and is principally defined by the body member 130 and the mounting wings 210(a), 210(b). The body member 130, however, preferably is somewhat flexible in nature, due both in part to its structure and to the material used to form the body member 130. Suitably rigid but flexible materials include, for example, but without limitation: plastics, polymers or composites such as polypropylene, polyethylene, polycarbonate, polyvinylchloride, acrylonitrile butadiene styrene, nylon, olefin, acrylic, polyester, as well as moldable silicon, thermoplastic urethane, thermoplastic elastomers, thermoset plastics and the like. However, other materials can be utilized.

The body member 130 and mounting wings 210(a), 210(b) are integrally formed to comprise a unitary retainer. This can be accomplished in any of a variety of ways well known to those skilled in the art. For instance, the entire retainer can be injection molded in order to reduce fabrication costs. The illustrated retainer 120 preferably is formed by injection molding using polyethylene or polypropylene material. The retainer, however, can comprise a non-unitary body member 130 and mounting wings 210(a), 210(b). In this manner, the body member and one or both of the mounting wings is formed separately and then coupled together. Additionally, the body member and mounting wings can have other forms and can have other orientations relative to one another. The body member 130 also can be clear or transparent to facilitate alignment of the retainer 120 with the catheter hub or other medical article during installation.

Each mounting wing 210(a), 210(b) preferably comprises a glue dam around a portion of its periphery on its underside. The glue dam restricts adhesive flow beyond an inner edge of the respective mounting wing. The outer edge of each mounting wing 210(a), 210(b) does not include the glue dam (as best seen in FIG. 11) to allow any excess glue or adhesive to seep out from under the mounting wing during the manufacturing process in the lateral direction away from the retainer 120.

The body member 130 of the retainer is attached to the upper surface 170 of the anchor pad 110 via the mounting wings 210(a), 210(b), as is shown in FIG. 2. The body member is desirably secured to the upper surface of the pad by a solvent bond adhesive, such as cyanoacrylate or other bonding material. One such adhesive is available commercially as Part No. 4693 from the Minnesota Mining and Manufacturing Company (now 3M).

When the anchor pads 110 are secured to the skin of the patient, the medical article is inhibited from moving substantially in either the lateral or transverse directions relative to the patient. Longitudinal movement of the medical article is inhibited by engagement between at least one abutment surface on the retainer 120 and a contact surface or mating surface on the medical article. The abutment surface on the retainer 120 preferably extends generally normal to the axis of the central channel 140. The abutment surface can be located at or between the distal and proximal ends of the retainer 120. For example, the abutment surface can be either the proximal or distal ends of the retainer (as will be apparent from the embodiments described later). Moreover, multiple abutment surfaces on the retainer 120 can be employed with each abutment surface being the same or a different type of abutment surface. Additionally, the abutment surface can be used to arrest movement in one longitudinal direction and the shape of the channel can be used to arrest movement in the opposite longitudinal direction. For example, at least a portion of the channel 140 can have a tapering inner surface and the retainer can include an abutment surface in the form of the proximal end of the retainer. The tapering shape and abutment surface cooperate to inhibit longitudinal motion in both longitudinal directions. In such an embodiment, the tapering surface contacts an outer tapering surface of the medical article to limit motion in one direction. Likewise, the proximal end of the retainer abuts with a radially extending member on the medical article to limit motion in the opposite direction.

The retainer 120 thus preferably includes one or more abutment surfaces. In the illustrated embodiment, the retainer includes multiple abutment surfaces that are formed by one or more slots 220 in the body member 130. In the form of a slot 220, one abutment surface forms one side of the slot and another abutment surface forms the other side of the slot 220.

To arrest longitudinal motion in the illustrated embodiment, two contact surfaces in the form of a single radially extending member are employed on the medical article. The radially extending member extends through the slot 220 in the retainer 120 to inhibit longitudinal motion of the medical article in both directions. The contact between the two abutment surfaces on the retainer and their corresponding contact surfaces on the medical article arrests motion in the longitudinal direction. Further embodiments of the retainer 120 inhibit rotational movement of the installed medical article. This will be discussed in greater detail below.

As shown in FIG. 5, the retainer 120 includes pairs of abutment surfaces with each pair forming one lateral slot 220 (preferably four abutment surfaces form at least two slots) that are sized to receive a radially extending portion of the catheter (e.g., a push tab that extends from a catheter hub). These slots 220 can extend circumferentially about at least a portion of the axis of the central channel 140. Each slot has a longitudinal length sufficient to accept the radially extending member of the retained medical article.

The radially extending portion of the medical article is preferably in the form of a push tab. An embodiment of a push tab is described with reference to FIGS. 15A and 15B. In particular, it can be desirable for the longitudinal length of each slot to be sufficient to receive the push tab 310 of the medical article; however, each slot 220 can be slightly larger than the push tab's thickness (as measured in the longitudinal direction) and a gap can exist between one or both sides of the push tab and the corresponding abutment surfaces that define the slot 220 into which the push tab has been inserted. In a preferred form, at least two or three annular slots 220 are disposed within the retainer 120. The longitudinal length of each slot 220 preferably is about five thousandths of an inch (0.005 inch, 0.127 mm) larger than the radially extending member (e.g., the push tab). Such an arrangement can be desirable to minimize longitudinal movement of the retained portion (e.g., the tab 310 in FIG. 15B) of the medical article. Accordingly, a small gap can exist between any abutment surface and a corresponding contact surface before the medical article is shifted relative to the retainer 120. Once shifted, however, further longitudinal movement is prevented by the interference between the contact surface and the abutment surface.

Those of skill in the art will recognize that each slot 220 need not have identical radial extent. The radial extent of each slot 220 need not be uniform about the axis of the central channel 140.

The inner edges of each slot 220 can be chamfered so as to ease the insertion of a radially extending member into any slot 220. By having the edges of each slot chamfered, it becomes possible to move a radially extending member 310 into a slot 220 even if the initial alignment between the center of the slot and the center of the radially extending member is not exact. The use of chamfered edges on the slots 220, as well as the presence of slots located at multiple longitudinal positions along the length of the central channel 140, allows for a medical article to be placed into the central channel of the retainer 120 with only coarse alignment with the axis of the central channel. The medical article generally moves into the nearest slot 220 as the medical article is pressed up into the retainer 120 from below (that is, as the retainer 120 is pressed over the retained portion of the medical article). The chamfered surfaces 240(a), 240(b) adjacent to the mounting wings 210(a), 210(b) help guide the medical article into the central channel 140. The alignment process is further facilitated when a portion of the retainer 120 is transparent.

Figure 13:
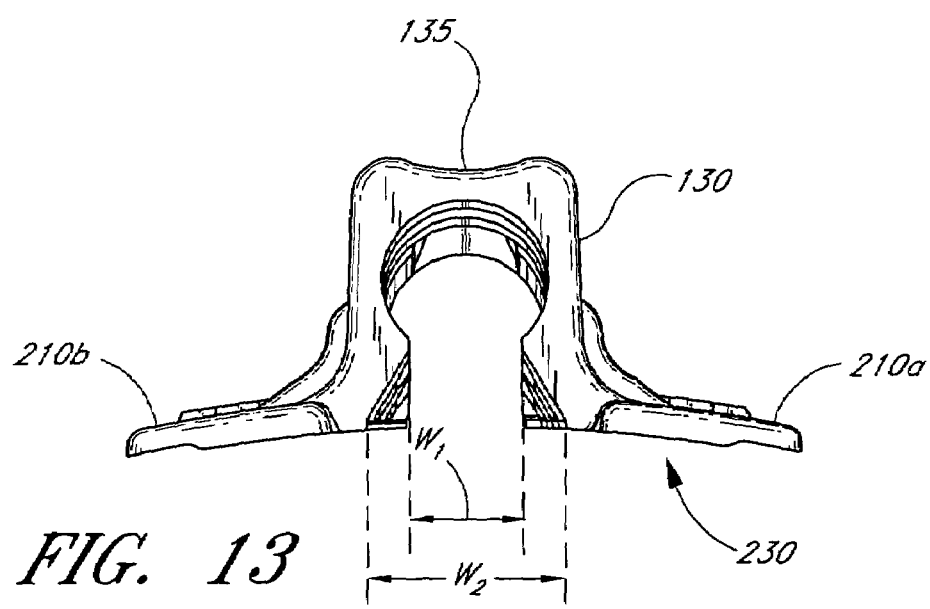
FIG. 13 is a rear side view of the retainer of FIG. 5.

As shown most clearly in FIGS. 6, 11, and 13, an upper section of the retainer 120 further comprises a depression 135 which forms a finger pad that a healthcare provider can press down upon. The depression 135 encourages the finger to push down on the retainer 120 and discourages the healthcare provided from gripping the retainer 120 on its sides during application. Such a side grip could squeeze or constrict the retainer 120 and make it harder to slip the retainer 120 over the medical article. By pushing down on the retainer 120, this constrictive effect is avoided.

As illustrated in FIGS. 6 and 13, a base surface 230 of the retainer 120 can have a concave curved shape when viewed from the front and rear sides. The degree of curvature can be varied depending on the expected location of usage or application of the securement device 100. It will be appreciated that many common sites for insertion of medical lines which require securement will be located on anatomical regions exhibiting convex curvature, such as a dorsal side of a hand, a arm, a leg, a contact surface, etc. By providing a concave bottom profile to the retainer 120, the retainer will rock less once placed upon the patient via the anchor pads 110(a), 110(b).

FIGS. 7 and 8 are side views of the retainer 120 of FIG. 5. As illustrated in FIGS. 7 and 8, an axis 260 of the central channel 140 lies at an angle with respect to the base surfaces 230 of the retainer 120. The desired angle between the medical article and the patient is created by angling the axis 260 of the central channel 140. This angle is selected in order to align the axis 260 of the channel 140 of the retainer with the desired incident angle with which the medical article is to contact the skin of the patient. A variety of different angles can be used, ranging from 0° to 45°, and more preferably from 5° to 25°. For instance, for the securement of intravenous catheters, it is desirable for the angle of incidence of the catheter to the skin of the patient to be between about 7° to about 15°. For the securement of arterial catheters, it is desirable for the angle of incident of the catheter to the skin of the patient to be about 12.5°. By angling the axis 260 of the channel 140 at the desired angle, which will depend upon the particular securement application (e.g., securing an arterial catheter, an intravenous catheter, etc.), the proper angle of incidence for a catheter can be maintained.

As illustrated in FIG. 5, the retainer 120 further comprises ribs 280. The ribs 280 project away from the outside surface of the channel 140. Such ribs may be formed by extending portions of the slots 220 of the retainer 120 away from the channel 140. The ribs 280 provide additional surfaces for the healthcare provider to grip the retainer 120.

As shown most clearly in FIGS. 5 and 7 through 10, located adjacent to the slots 220 are upper sections 250. The thickness of the upper sections 250 in the longitudinal direction can vary in order to maintain a generally constant spring force along the entire length of the retainer 120. In this way, the same amount of force is required to spread the walls of the retainer 120 apart even though in the illustrated embodiment the back end of the retainer 120 spreads more to receive the larger diameter section of a tapered catheter hub. As illustrated in the cross-section views of FIGS. 9 and 10, the longitudinal and transverse lengths of the upper sections 250 vary between one or more of the upper sections.

Although certain features of the retainer 120 can be specifically configured for use with a catheter hub, it will be understood by those of skill in the art that such a retainer 120 can be used with other adaptors or medical lines as well. Furthermore, the retainers described herein can be modified to more effectively cooperate with various types of connector fittings and adaptors.

As shown in FIGS. 5 through 13, each slot 220 is substantially annular in form. However, as illustrated most clearly in FIG. 11, a stop member or wall 290 preferably extends into the path of the one or more slots 220 at a circumferential location about the axis of the central channel 140. A comparison of FIGS. 9 and 10 illustrates that the wall 290 in the illustrated embodiment is located on the mounting wing 210(b) side of the retainer 120. As shown in FIG. 11, the wall 290 in the illustrated embodiment extends in a lateral direction away from the mounting wing 210(b) and into one or more slots 220. In this way, the wall 290 limits the rotation of the radially extending member and medical article when the medical article is installed in the retainer 120. Thus, in the illustrated embodiment, one or more slots 220 extend circumferentially about the axis of the central channel 140 for less than 360 degrees.

The wall 290 can be located at other locations around the circumference of the central channel 140. For example, the wall 290 could extend in a lateral direction away from the mounting wing 210(a) and into one or more slots 220. In embodiments of the retainer 120 where the wall 290 extends into less than all of the slots 220, the healthcare provider can select whether to restrict the rotation of the medical article. For example, the healthcare provider can restrict the rotation of the medical article by inserting a radially extending member of the medical article into a slot 220 that includes the wall 290. Alternatively, the healthcare provider can install the radially extending member into a slot 220 that does not include the wall 290 to allow unbridled rotation of the medical article. Moreover, more than one wall 290 can be located around the circumference of the one or more slots 220 to further limit the rotation of the medical article. In still further variations of the retainer, the retainer can omit the wall(s) 290.

Each slot 220 preferably has a lateral width sufficient to receive the radially extending member of the medical article. In this way, the retainer 120 is designed to grip non-winged catheters regardless of the position of the radially extending member. For example, in the illustrated embodiment, a catheter hub can be installed into the retainer 120 regardless of rotation of the catheter hub about its axis except when the catheter hub is rotated such that the radially extending member coincides with the wall 290. The slot 220 can initially receive the radially extending member whether the radially extending member is pointing away from the patient, toward the patient, to either side, or generally at any other angle about the axis of the catheter hub. However, when the radially extending member is pointing directly to the left side and the catheter hub enters the opening 150, the radially extending member contacts the wall 290. As the catheter hub is further installed into the retainer 120, the catheter hub is forced to rotate such that the radially extending member is pointing downward. When the radially extending member is pointing downward, the radially extending member will follow the catheter hub into the retainer 120 as the catheter hub is inserted through the opening 150. Once the catheter hub has rotated and is subsequently fully installed in the retainer 120, the wall 290 will not allow the catheter hub and radially extending member to rotate completely about the axis of the central channel 140. For example, as the catheter adapter is rotated, the radially extending member of the catheter hub slides within the slot 220. However, at some point during the rotation of the catheter hub, the radially extending member contacts the wall 290.

In the embodiment illustrated in FIGS. 5 through 13, the wall 290 limits the rotation of the radially extending member when the push tap is sufficiently rotated in either direction towards the mounting wing 210(b) side of the retainer 120. In this way, the wall 290 prohibits the catheter hub from 360-degree rotation while the catheter hub is installed in the retainer 120.

When the radially extending member points downward (e.g., toward the patient) and generally normal to the bottom surfaces of the retainer 120, the radially extending member extends through the lower opening 150. The hips 270 in the lower opening 150 are spaced sufficiently close to capture the radially extending member in this position and thereby inhibit longitudinal movement of the catheter hub.

FIG. 12 is a bottom plan view of the retainer 120 and illustrates that the distance between the side mounting wings 210(a), 210(b) varies in the region of the retainer 120. Width W1 is measured between the side mounting wings 210(a), 210(b) in a lateral direction as shown. Width W2 is measured between the side mounting wings 210(a), 210(b) in a lateral direction as shown. FIG. 13 is a rear side view of the retainer 120 and further illustrates the widths W1 and W2 from FIG. 12. The side mounting wings 210(a), 210(b) are designed so that width W1 is less than the width W2. Width W1 is selected to deter backward insertion of the medical article into the retainer 120. For example, the width W1 could be selected to be smaller than a spin nut or the connector end of the catheter hub. With W1 less than W2, the potential for the medical article being incorrectly inserted into the retainer 120 is reduced.

Medical Articles

Figure 15A:
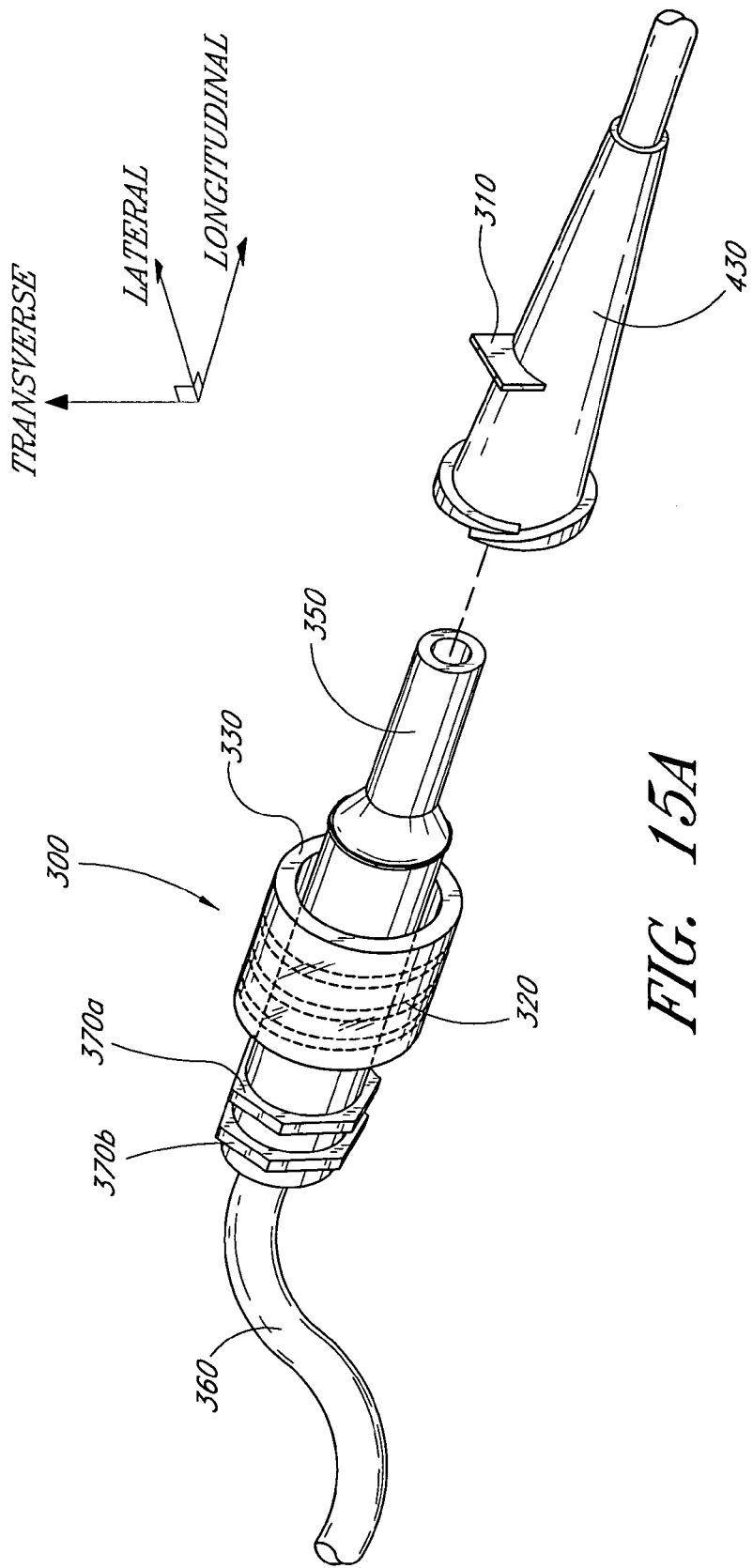
FIG. 15A is a perspective view of an example of a connector fitting with a spin nut and of a catheter hub with which the securement device of FIG. 1 can be used.

An exemplary medical article for use with the embodiment of the securement device described above will now be described with reference to FIGS. 15A and 15B. The medical article can be a single medical article or a combination of one or more medical articles. Such medical articles can be or include, for example, but without limitation, connector fittings, catheters, catheter hubs, catheter adaptors, fluid supply lines, or other similar articles. FIG. 15A is a perspective view of a catheter hub 430 and a connector fitting 300 with a spin nut 330. The connector fitting 300 is preferably disposed upon the end of a medical line 360 which can be connected to a drip bag, blood monitor, or other fluid related medical apparatus. While the retainer 120 of FIG. 2 is configured to receive a portion of the catheter hub 430, the retainer can be configured for use with the connector fitting 300, as will be described8.

The connector fitting 300 comprises an elongated body 320 which is attached to the end of the medical line 360. The connector fitting 300 also comprises a portion that is tapered along at least part of its longitudinal length so as to allow the end of this region to fit within the tapered conical portion of an catheter hub 430. The tapered portion 350 of the connector fitting 300 also preferably includes a centrally disposed lumen that communicates with the lumen of the medical line.

Figure 15B:
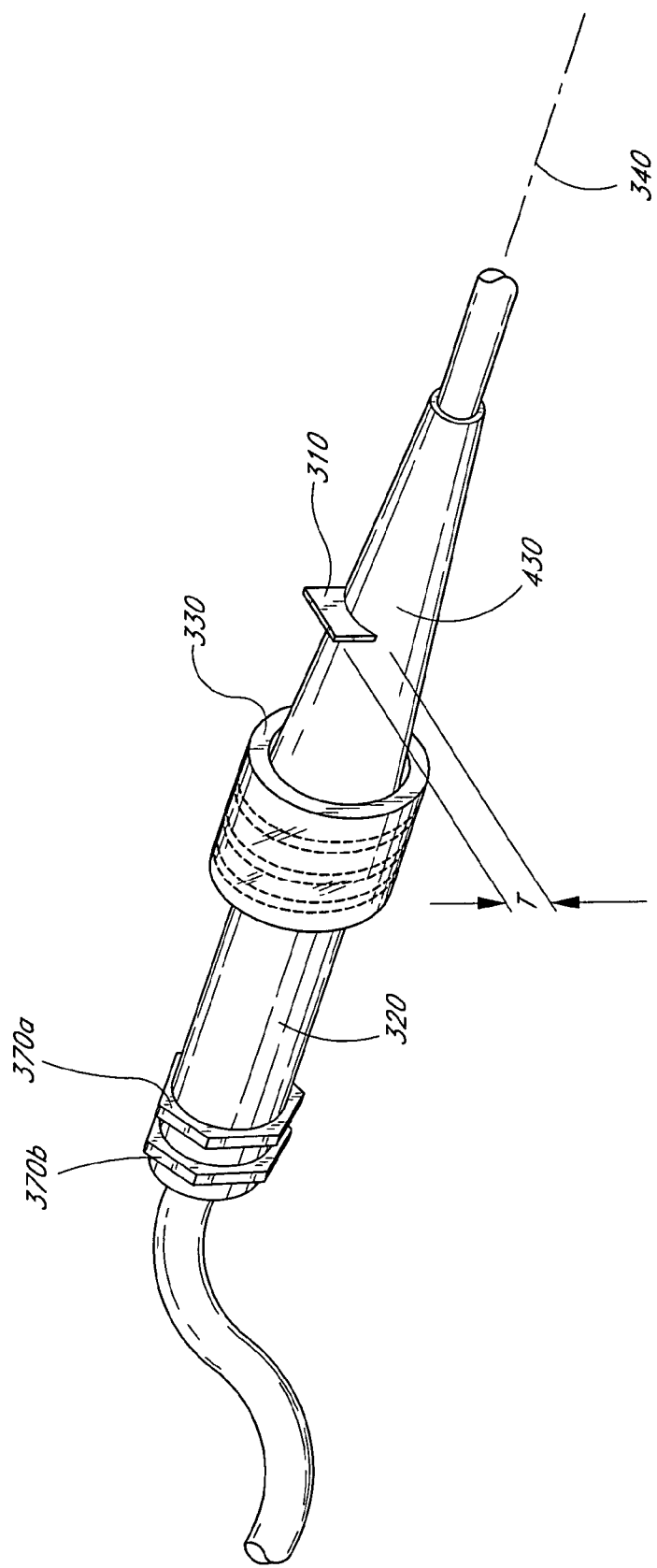
FIG. 15B is a perspective view of the connector fitting of FIG. 15A with the spin nut secured in the forward position and secured to the catheter hub.

FIG. 15B is a perspective view of the connector fitting 300 of FIG. 15A with the spin nut 330 secured in the proximal position and secured to the catheter hub 430. When the connector fitting 300 is inserted into the catheter hub 430, the lumen of the connector fitting is disposed in fluid communication with the lumen of the catheter hub 430. This provides fluid communication between the medical line 360 and the patient.

As seen in FIGS. 15A and 15B, the connector fitting 300 has at least two contact surfaces in the form of one radially extending element 370(a) disposed upon an end of the elongated body 320 of the connector fitting 300 opposite the tapered end 350. It may be advantageous for the radially extending element 370(a) to extend completely around the circumference of the connector fitting 300. Additional contact surfaces in the form of a second radially extending element 370(b) can also be disposed upon the elongated body 320, as can additional radial elements (not shown). Those of skill in the art will recognize that the radially extending element or elements 370(a) need not have any particular shape or longitudinal thickness. Additionally, the radially extending elements need not have the same shape. For instance, the first radially extending element 370(a) can have the hexagonal shape illustrated and the second radially extending element 370(b) can have a circular shape.

A spin nut 330 is disposed upon the connector fitting 300 around the elongated body 320 of the fitting. The spin nut 330 is substantially cylindrical in form and is able to move upon the connector fitting 300. The spin nut 330 is capable of both rotational motion around the axis of the connector fitting and axial motion in both the proximal and distal directions along the length of the elongated body 320 of the fitting. The spin nut 330 also includes internal screw threads which are illustrated with phantom lines in FIGS. 15A and 15B.

Still referring to FIGS. 15A and 15B, an catheter hub 430 includes a body that, in the illustrated embodiment, is configured as a catheter hub and has a generally conical shape and tapers from a large radius to a smaller radius along its length. In the illustrated embodiment, the catheter hub 430 comprises two contact surfaces that together form a radially extending member. The radially extending member can be, for example, a lateral tab 310 which is disposed at a position along the length of the body of the hub. The tab 310 can be gripped by the healthcare provider from the upper side of the retainer 120 in order to immobilize the catheter hub 430 when unscrewing the spin nut 330 or otherwise disengaging the connector fitting 300 from the catheter hub.

The catheter hub 430 also can include an external screw thread on the outside of the conical body near the end with the larger radius. The screw thread can be used in association with the spin nut 330 of the connector fitting 300 in order to securely interconnect the connector fitting 300 and the catheter hub 430.

The at least one retention surface 165 supports the medical article so that the medical article is elevated in the retainer 120 such that the retained portion of the medical article (e.g., the retained portion of the catheter hub) is raised from the patient's skin to lessen or eliminate compression, excoriation, and/or chaffing of the skin. Thus, the retainer 120 lifts and holds the retained portion of the catheter hub up from the patient's skin.

With reference to FIG. 11, dimensions L1 and L2 illustrate how the wall 290 described above prohibits 360-degree rotational movement of the catheter hub 430 when the catheter hub 430 is installed in the retainer 120. Referring to FIGS. 11 and 15, when the catheter hub 430 is fully installed in the retainer 120, the push tap 310 extends in a direction away from the central axis 340 of the catheter hub 430 and into the slot 220. As shown in FIG. 15B, a maximum distance from the central axis 340 to a distal end of the push tab 310 is distance T. With reference to FIG. 11, to allow the push tab of the catheter hub 430 to rotate in the region of the mounting wing 210(a), a distance L1 is selected to be equal to or greater than the distance T. The distance L1 is measured between the axis of the central channel 140 and the top surface of the mounting wing 210(a) as shown in FIG. 11. Selecting L1 to be greater than the distance T permits the push tab 310 to rotate past the mounting wing 210(a).

In contrast, to limit rotation of the catheter hub 430 and push tab 310 in the region of the mounting wing 210(b), a distance L2 is selected to be less than the distance T. The distance L2 is measured between the axis of the central channel 140 and the top surface of the wall 290 as shown in FIG. 11. Selecting L2 to be equal to or preferably less than the distance T does not permit the push tab 310 to rotate past the mounting wing 210(b).

An advantage of limiting the rotation of the catheter adapter 430 when it is installed in the retainer 120 can be understood with reference back to FIG. 15B. In FIG. 15B, the connector fitting comprises an elongated body 320 which is attached to the end of a medical line. The other end of the elongated body 320 connects to the catheter adapter or hub 430. The push tab 310 is disposed at a position along the length of the body of the hub. A spin nut 330 is disposed around the elongated body 320 of the fitting. Internal screw leads within the spin nut 330 engage with an external screw thread on the catheter hub 430 in order to securely interconnect the connector fitting and the catheter hub 430.

With reference to FIGS. 5 through 13, since the push tab 310 will contact the wall 290 of the retainer 120 when the spin nut is rotated less than 360 degrees, once the push tab 310 contacts the wall 290, the healthcare provider can connect or disconnect the elongated body from the catheter adapter 430 without having to also grip the tab 310. Once the healthcare provider rotates the fitting in either direction so that the tab 310 contacts the wall 290, the catheter hub 430 is effectively immobilized in that direction such that further rotation of the catheter hub 430 in that direction is prohibited. Once immobilized, the healthcare provider can unscrew the spin nut 330 or otherwise disengage the connector fitting from the catheter hub with a single hand. While the use of two hands may be advantageous in certain circumstances when operating the spin nut 330, the retainer 120 allows the healthcare provider to use a single hand.

Similarly, when connecting or re-connecting the elongated body to the catheter hub, the healthcare provider can initially rotate the push tab, via the spin nut, until the push tab contacts the wall 290. Once the push tab contacts the wall 290, the catheter hub is immobilized which can enhance further connecting of the elongated body to the catheter hub. In this way, the healthcare provider can continue to turn the spin nut until the spin nut is fully engaged with the catheter hub without having to grip the push tab or catheter hub.

The retainer 120 can be used with both luer slip and luer lock connector fittings. The retainer 120 is designed such that even with the push tab 310 positioned in the forward most slot 220, the retainer can fit in the space defined between the push tab 310 and the spin nut 330 with the spin nut fully engaged. The retainer 120 can be further sized to closely fit within this space to provide redundancy in arresting longitudinal movement of the catheter hub 430 relative to the retainer 120. Such slots 220 can also be disposed to extend longitudinally to accommodate radially extending members of greater longitudinal length, such as the splines of a Kipp-style connector.

Operation

An exemplary process for coupling a medical article with the securement device described above will now be described with reference to FIGS. 16 through 18.

A preferred method of using the preferred embodiment of the securement device illustrated in FIGS. 1–13 will be described in the context of starting an intravenous line. However, the aspects and features of the operational method and the use of the present securement device is not limited to this particular application.

A heathcare provider preferably begins the procedure by inserting an IV catheter into patient's vein in a known manner and then attaching an intravenous line to the IV catheter though the luer connection. In particular, the healthcare provider inserts the tapered or luer end 350 of the connector fitting 300 into the catheter hub 430 and then turns the spin nut 330 to thread the spin nut 330 over a thread flange disposed at the distal end of the catheter hub 430. This action draws together the two medical article components and releasably interlocks them. The immediate connection of the IV line to the catheter inhibits a back flow of blood through the catheter. The healthcare provider now preferably secures the IV catheter in place on the patient using the securement device 100. In some variations of this method, however, the securement device 100 can be first be attached to one or both of the medical article (as well as the possibly to the patient) before the healthcare provider makes the connection between the two medical articles.

In order to illustrate more clearly the interaction between the retainer 120 and the catheter hub 430 in this embodiment, the anchor pads 110(*a*), 110(*b*) of the securement device 110 are illustrated as detached from the retainer 120. In accordance with the preferred embodiment, however, the entire securement device 100 is assembled in accordance with the above-description (e.g., the mounting wings 210 are attached to the anchor pads) and is sterilized before use.

Figure 16:
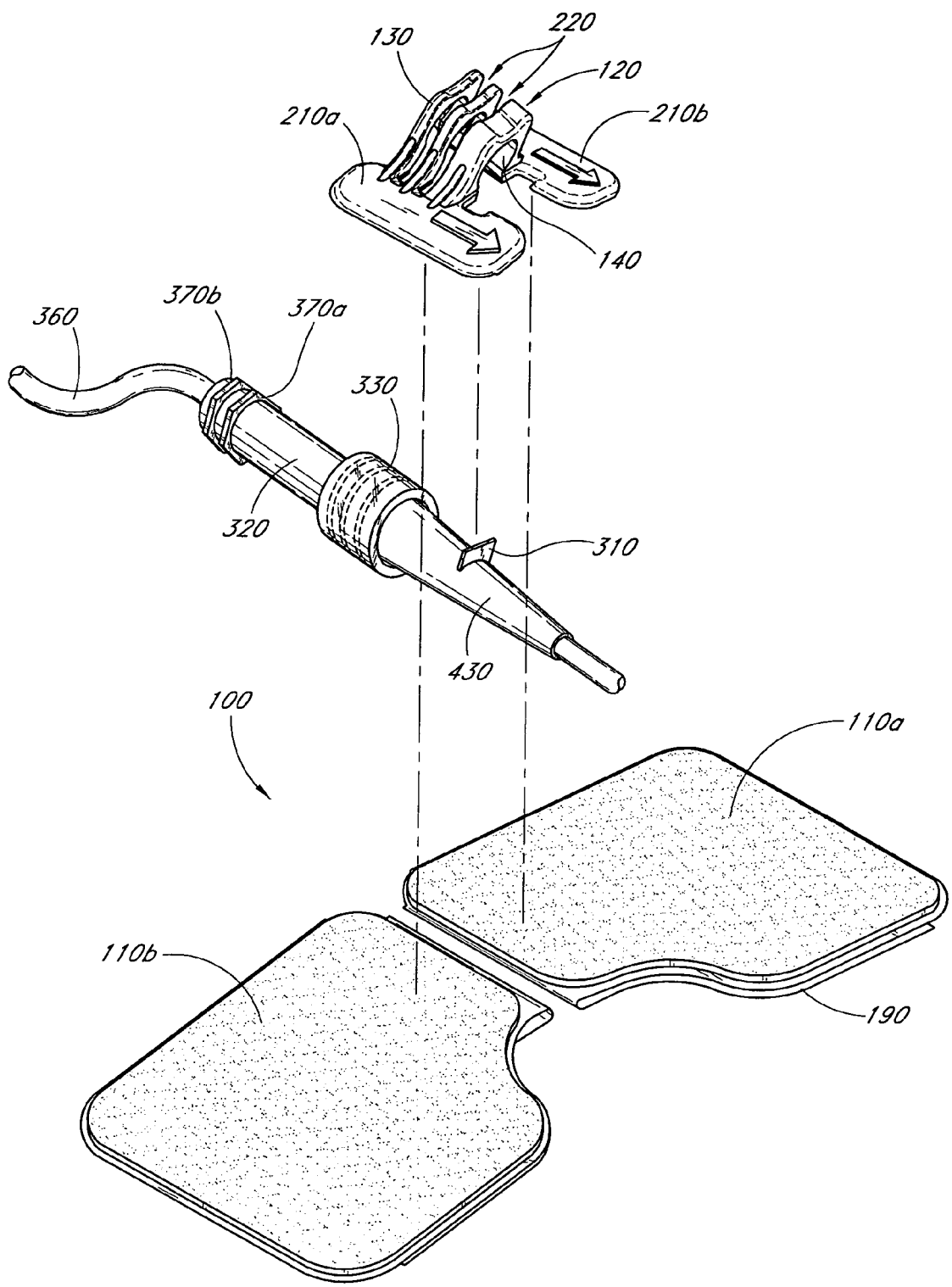
FIG. 16 is an exploded, perspective view of the connector fitting secured to the catheter hub of FIG. 15B, both aligned with the anchor pad and the retainer of FIG. 1.

FIG. 16 is a perspective view of the connector fitting 300 secured to the catheter hub 430, both aligned with the anchor pad 110(*a*), 110(*b*) and the retainer 120. Healthcare provider can secure a medical line 360 and the medical articles to a patient using the above-described securement device 100 or a readily apparent modification thereof. The healthcare provider aligns the central channel 140 of the retainer 120 over the adaptor or catheter hub 430.

Figure 17:
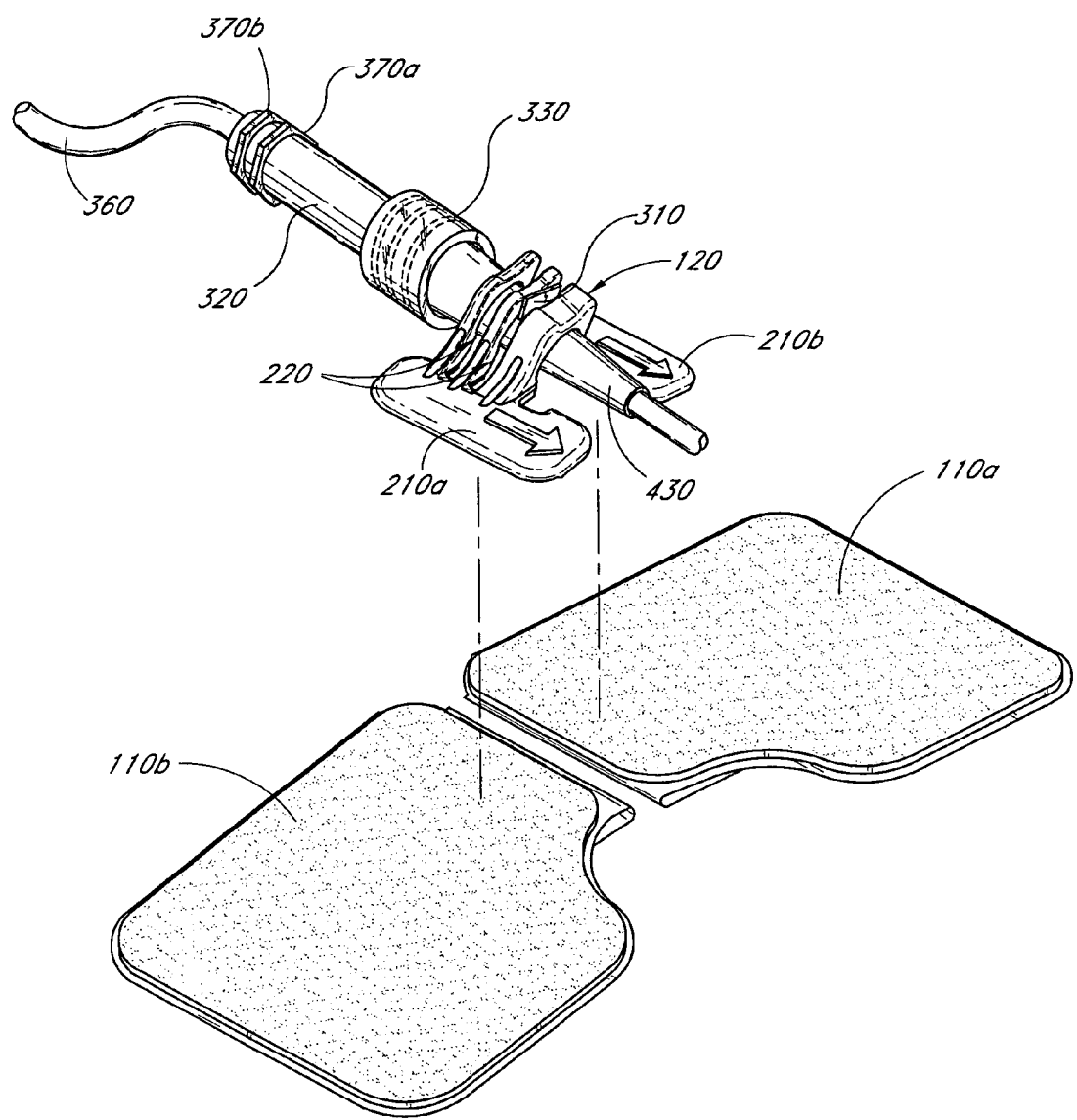
FIG. 17 is an exploded, perspective view of the connector fitting secured to the catheter hub of FIG. 15B, with the catheter hub being inserted into the retainer of FIG. 1.

FIG. 17 is a perspective view of the connector fitting 300 secured to the catheter hub 430 with the catheter hub being inserted into the retainer 120. The lower opening 150 in the retainer 120 is pressed over the catheter hub 430 whereby the catheter hub fitting slides into the central channel 140 of the body member 130. Depending on the diameter of the catheter hub 430, the retention surface 165 can provide a snap-fit connection between the hub and the body member 130. The contact surfaces of the catheter hub preferably form one or more radially extending members 310 (e.g., one or more push tabs or annular collars), as shown in the illustrated embodiment. The radially extending member(s) fits into one (or more) of the lateral slots 220 in the retainer. As can be seen, the tab 310 of the catheter hub 430 lies within one of the slots 220 of the retainer 120. In addition, the body of the catheter hub 430 generally lies within the central channel 140 of the retainer. When guided through the lower opening 150 by the healthcare provider, the body of the catheter hub 430 will lie within the central channel 140 of the retainer 120. The abutment surfaces of the slot 220 will inhibit longitudinal migration of the catheter hub 430 through the central channel 140 of the retainer 120.

In addition, if used with a connector fitting 300 in which a portion of the connector fitting, such as the spin nut 330, has a greater radial size than the size of the central channel 140 of the retainer 120, the spin nut 330 can act as a contact surface and will inhibit axial motion in one direction through the central channel 140 of the retainer as well. Using the size of the spin nut 330 or other element having greater radial size than the size of the channel is not required for effective operation of the systems described herein; however, such a technique may be an effective form of securement or redundant securement in some applications.

The combination of the channel shape 140 (both the truncated circular shape and the tapering width), the top of the retainer, and the interengagement between the slot(s) 220 and the radially extending member(s) 310 on the catheter hub 430 arrest movement of the retained section of the medical line in three dimension: longitudinally, laterally and transversely. Further, the wall 290 in the illustrated embodiment prohibits the catheter hub from 360-degree rotation while the catheter hub is installed in the retainer 120. The rotational stop provided by the wall 290 allows the heathcare provider to attach and detach the spin nut (and thus the connector fitting) to and front the catheter hub without having the remove the catheter hub from the retainer. While this feature is preferred in the illustrated application, it is optional and the wall 290 can be omitted from the securement device, as noted above.

Figure 18:
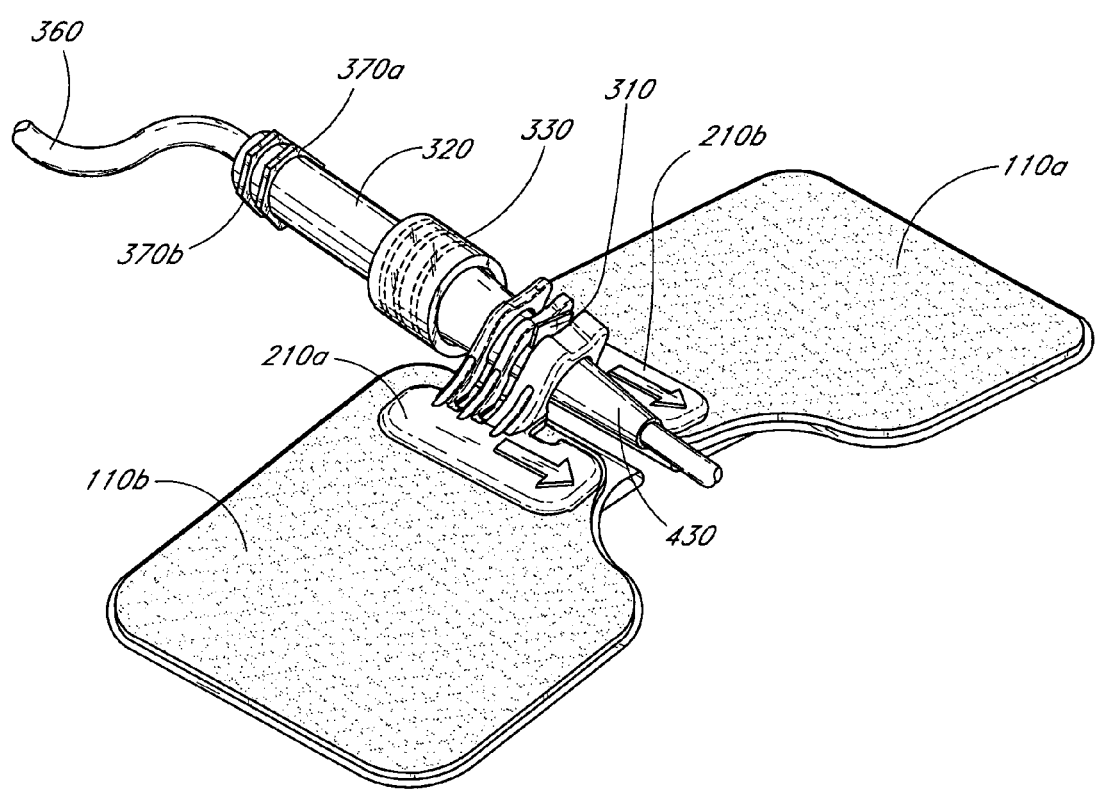
FIG. 18 is a perspective view of the catheter hub secured to the securement device of FIG. 1.

FIG. 18 is a perspective view of the retainer 120 attached to the anchor pads 110 and securing the catheter hub 430 therein. Once the catheter hub or other medical article enters the lower opening 150 of the retainer 120, the anchor pads 110(*a*), 110(*b*) are secured to the patient. The central channel 140 of the retainer surrounds an arc length of more than 180 degrees of the medical article. This inhibits any transverse or lateral motion of the medical article relative to the retainer 120. The catheter hub can be inserted into the retainer either before or after the fitting connector is attached to the hub.

The healthcare provider can first remove one portion of the release liner 180 from the anchor pad 110 by gripping the pull tab 190 and pulling the liner 180 away from the lower surface 160 of the anchor pad 110. This exposes the adhesive layer of the anchor pad, which can then be applied to the skin of the patient near the site where the healthcare provider desires to secure the connector fitting 300 or other medical article. The adhesive layer of the second anchor pad which is located in a lateral direction from the first anchor pad can be similarly exposed. The remainder of the release liner 180 for the first and second anchor pads can then be removed and the anchor pad fully attached to the skin of the patient. As a variation, the release liner on one anchor pad can be pulled away and the anchor pad can be fully attached to the patient before attaching the second anchor pad to the patient.

Additional Embodiments

As understood from the above description of the securement device embodiment shown in FIGS. 1–13 and 16–18, the securement device 100 arrests longitudinal movement of the retained section of the catheter hub 430 by interacting with at least one and preferably two contact surfaces of the tab 310, which constitutes a radially extending member in the illustrated embodiment. This approach for arresting longitudinal movement can also be used with other types of radially extending members or contacts (e.g., contact surfaces) on the catheter hub 430, the connector fitting 300 or other medical articles or components thereof. For example, a retainer can be configured to capture or receive a tab, spline (e.g., a longitudinally extending spline) or collar on the connector-fitting that is disposed on the distal side of the spin nut 320, or can capture all or a portion of the spin nut. In other embodiments, the retainer can be configured to fit between contacts on a medical article or medical articles. For example, the retainer can be sized to fit between the spin nut 320 and the hexagonal collar 370 on the connector fitting 300 or between the proximal side of the spin nut 320 and the distal side of the catheter hub tab 310. In such cases, the end surfaces of the retainer function as the abutment surfaces and cooperate with adjacent contacts on the medical article (s). Additionally, the retainer can be configured to not only fit between two contacts on the medical article(s) but also can be configured to receive one or more radially extending members of the medical article(s).

In a variation of this approach, longitudinal movement can also be fully arrested (i.e., arrested in both directions along the longitudinal axis) by (1) the interaction of an abutment on the retainer and a distally facing contact in combination with (2) the shape of the channel 140. For example, in the previously discussed embodiment, the tapering shape of the channel 140, which decreased in size in the proximal direction, inhibited longitudinal movement toward the insertion site. The interaction between a proximal side wall of the slot 220 and the distal side of the catheter hub tab 310 prevents longitudinal movement in the distal direction. Thus, some embodiments need only include one abutment. As noted above, the channel can have a tapering shape along at least a portion of its length and a step down in diameter along its length (as best illustrated in FIG. 14B). The tapering shape can arrest longitudinal movement in one direction and an abutment, which is formed at the diameter step down, can interact with a corresponding contact (e.g., contact surface) on the medical article to arrest longitudinal movement in the opposite direction.

Several variations of the retainer design are described below in connection with FIGS. 19–28. These retainer designs cooperate with contact points or surfaces on the connector fitting 300 to arrest movement in the longitudinal direction. Depending on what contact points or surfaces are provided on the connector fitting 300, (for example, radially extending members, spin nuts, collars, tabs), one or more abutments on the retainer will generally abut against one or more of the contact points or surfaces (as noted above a slight gap can occur in some applications). Additional or redundant abutment points or surfaces may be provided.

Figure 21:
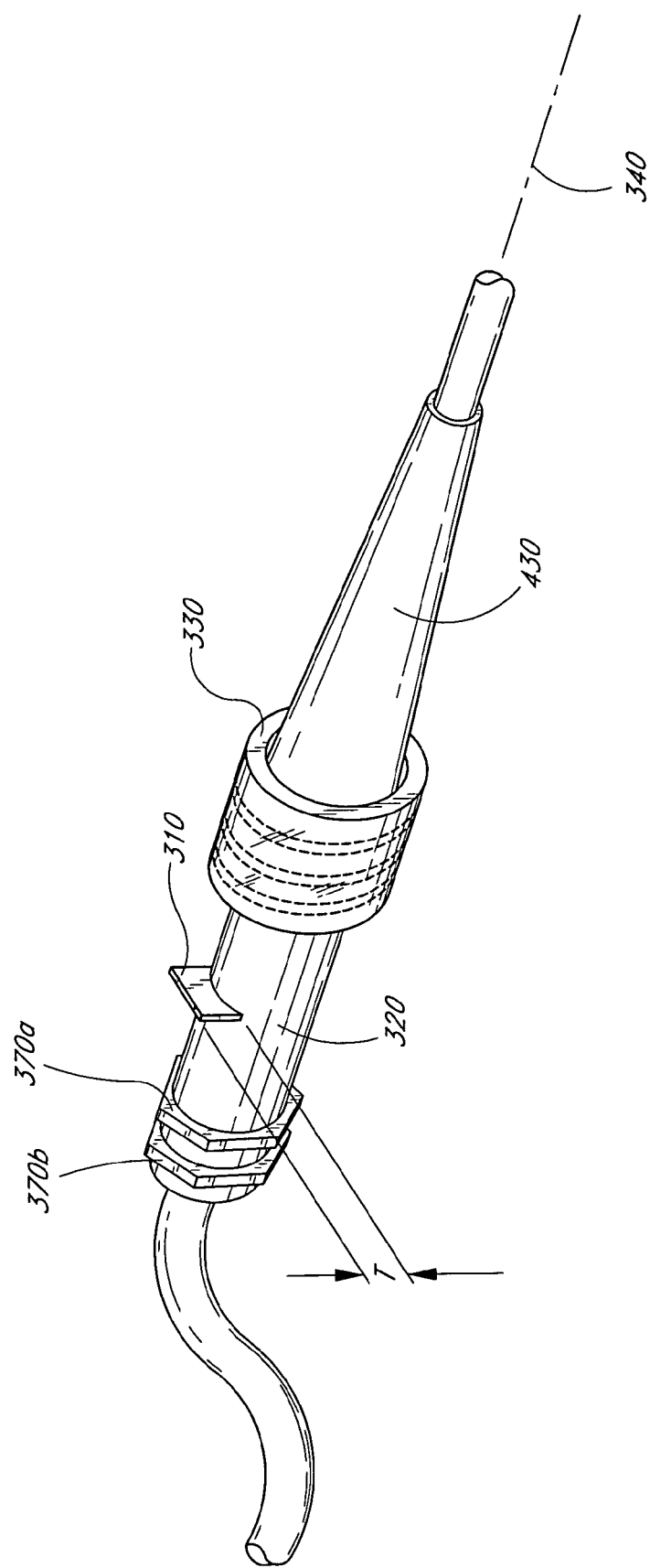
FIG. 21 is a perspective view of another connector fitting secured to a catheter hub, with the connector fitting having a radially extending tab.
Figure 22:
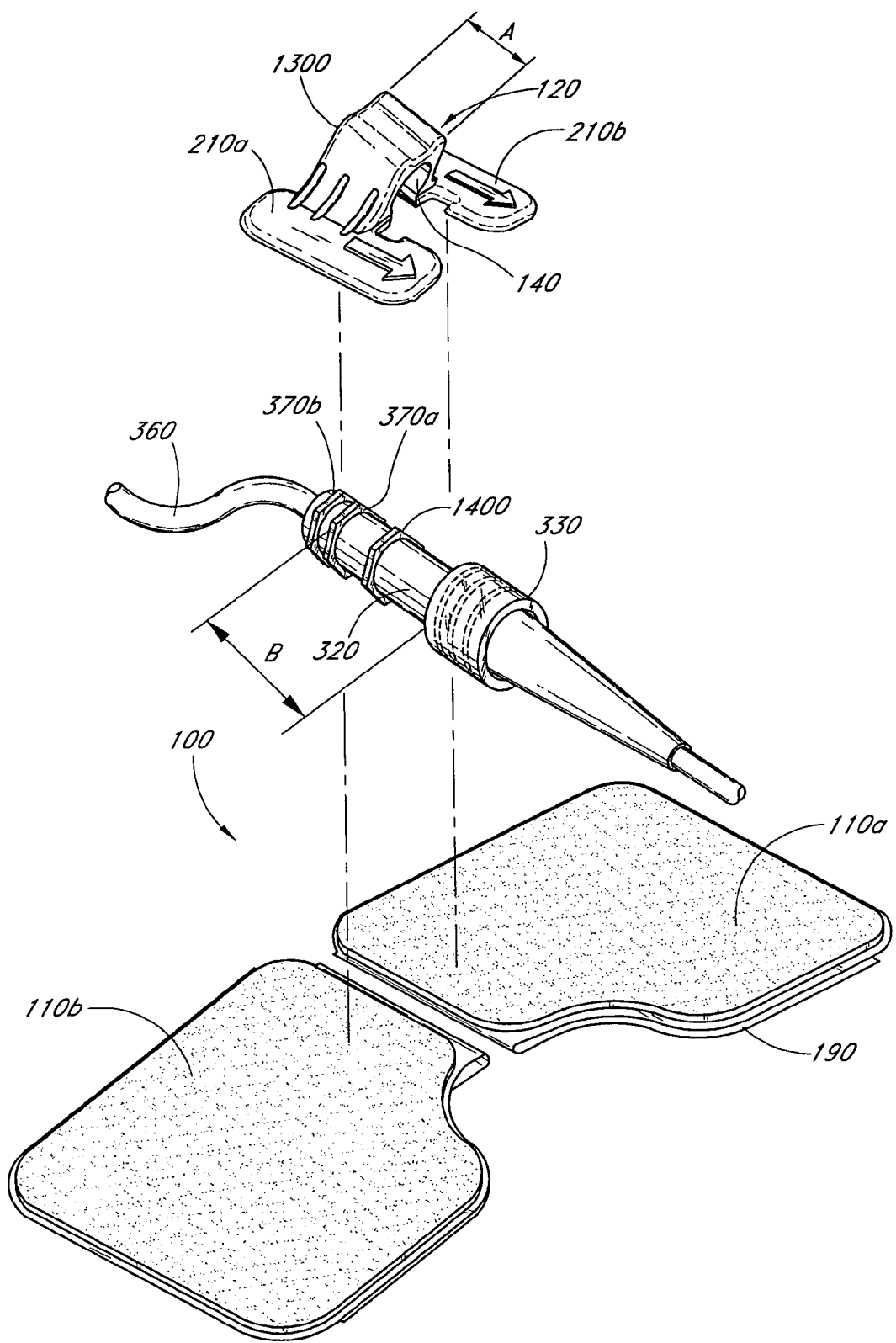
FIG. 22 is an exploded, perspective view of the connector fitting and the catheter hub of FIG. 20, the collar of the connector fitting being aligned with the anchor pad and the retainer of FIG. 19.

One embodiment (FIG. 19) illustrates a retainer 120 designed to fit between the spin nut 330 and a hexagonal collar 370a on the connector fitting (FIGS. 20 and 21) as shown in FIG. 22. In this embodiment, the distal and proximal ends of the retainer 120 are the abutment surfaces.

Figure 19:
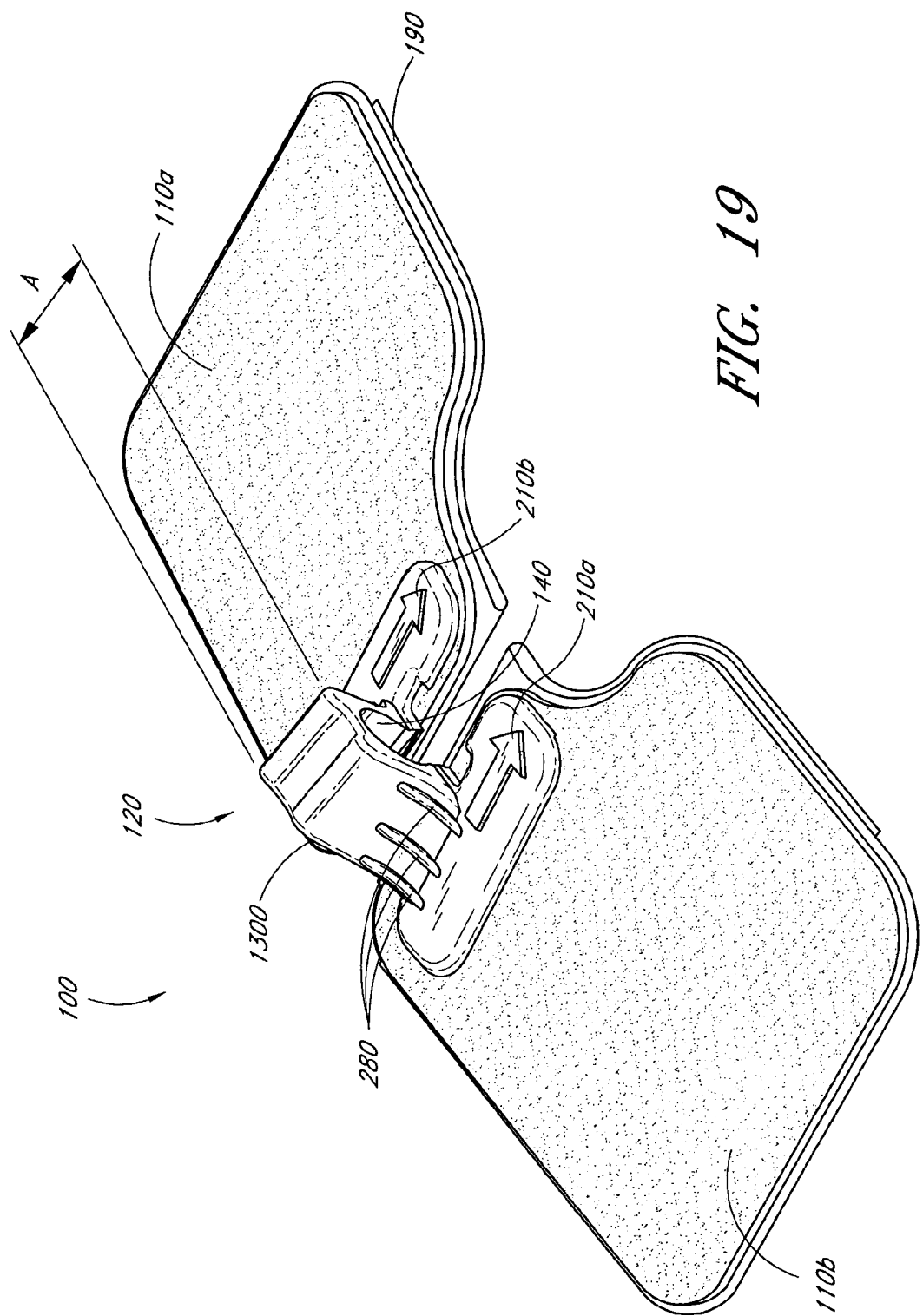
FIG. 19 is a perspective view of a securement device configured in accordance with another preferred embodiment of the present invention.
Figure 20:
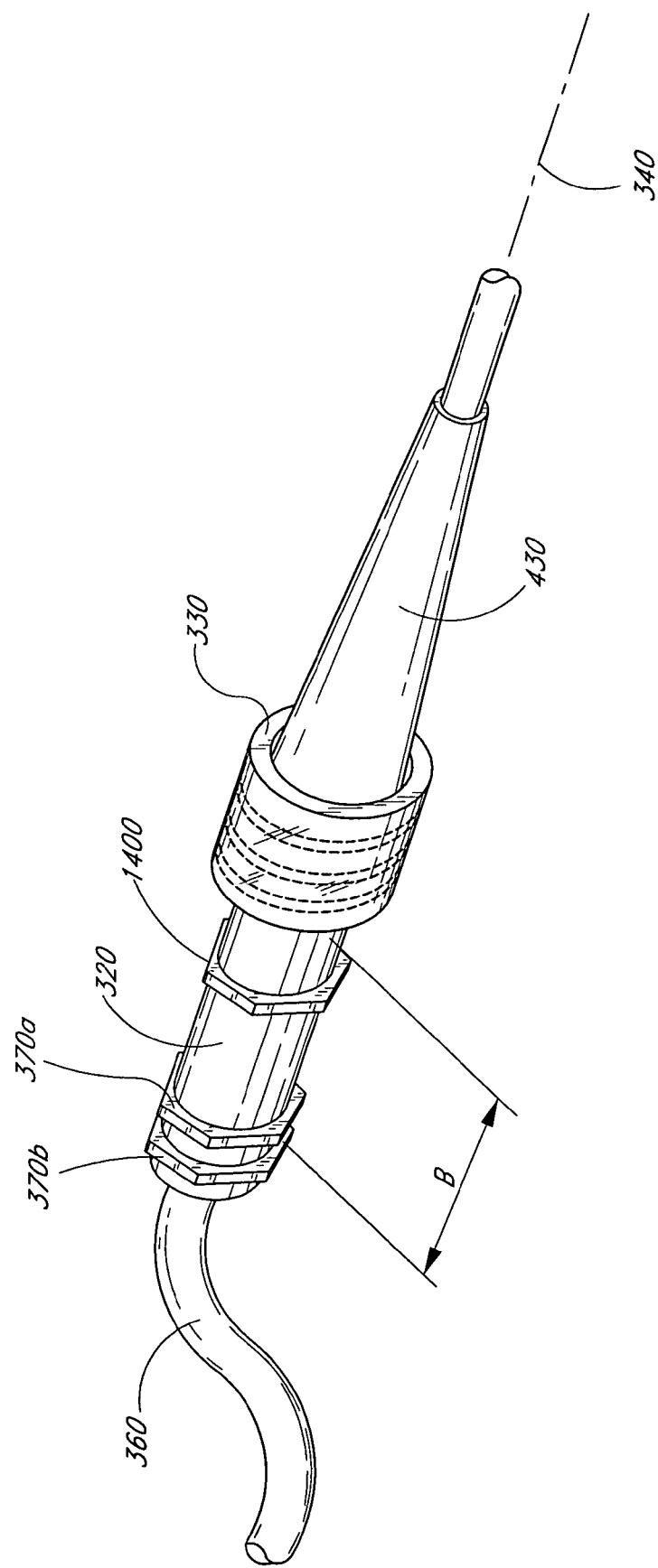
FIG. 20 is a perspective view of a connector fitting secured to a catheter hub, with the connector fitting having a first collar located between a second collar and a spin nut.
Figure 26:
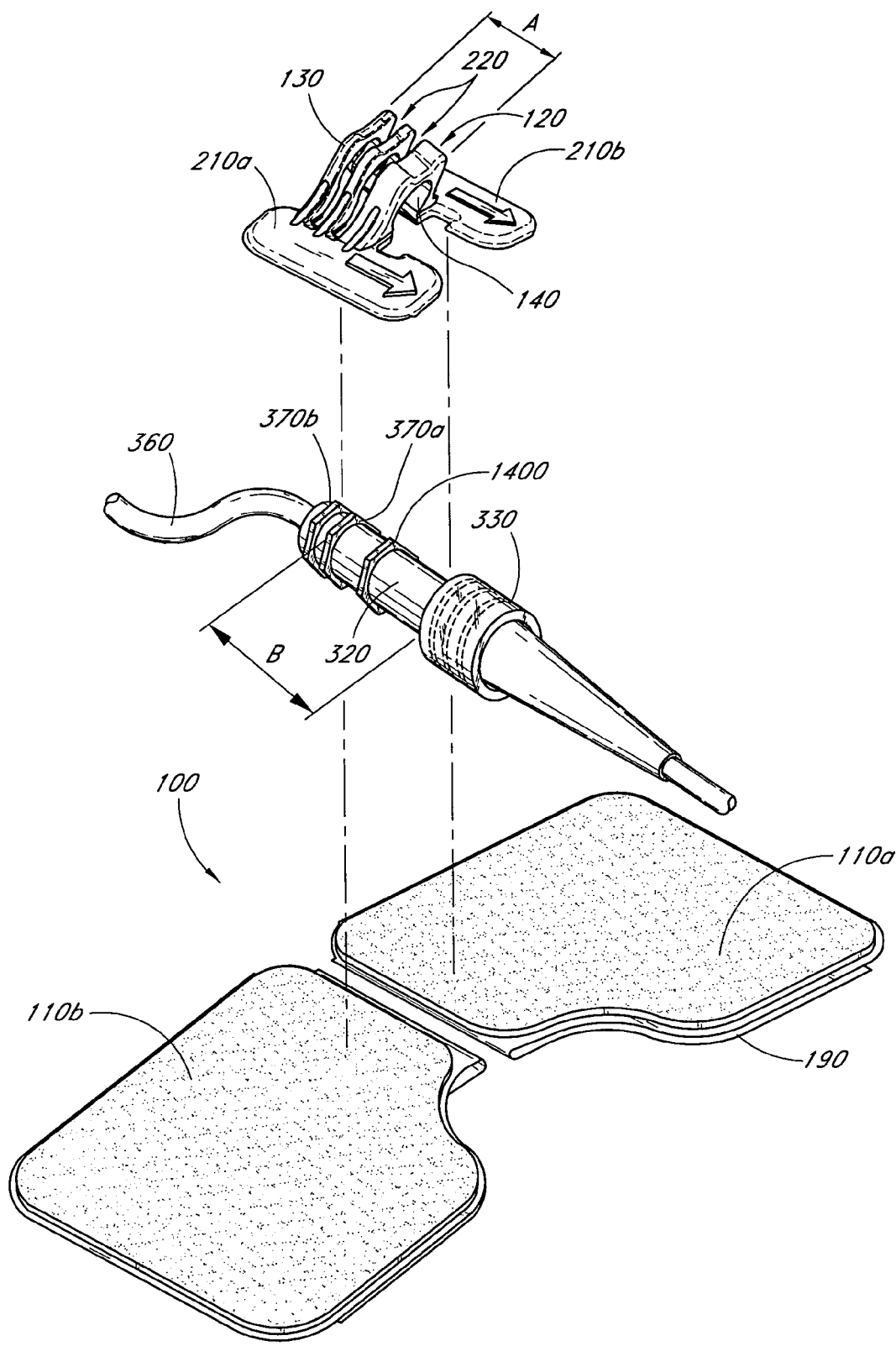
FIG. 26 is an exploded, perspective view of the connector fitting and the catheter hub of FIG. 20, the connector fitting being aligned with an anchor pad and a retainer of the securement device of FIG. 1.

Additionally, the body member 1300 in this embodiment may or may not include a groove, slot or other receptacle in the channel 140 for receiving a ring 1400 or connector tab 310 (FIGS. 20 and 21). Moreover, depending on the radial extent of the ring 1400 or connector tab 310, such a groove, slot, or receptacle may or may not extend through the wall of body member 1300. The retainer previously described with reference to FIGS. 1–13 incorporates such a groove, slot, or receptacle in the form of a slot 220 for engaging with the catheter hub 430 (see FIG. 18). This slot 220 extends through the wall of the retainer. To illustrate how a groove, slot, or receptacle in the body member 1300 (FIG. 19) would engage with a radially extending member on the connector 300, one of the slots 220 in the retainer from FIGS. 1–13 is shown in FIG. 26 as being aligned with a hexagonal nut 1400 on the connector body 320. Once installed, the hexagonal nut 1400 can abut against the proximal and distal abutment surfaces of the slot 220. By providing a groove in the channel 140 of the body member 1300, motion of the retainer can be further inhibited by the interaction of the groove with the ring or tab. Even if a groove(s) is not provided in the retainer illustrated in FIG. 22 and the channel 140 does not fit flush against the connector body 320, partial contact between the abutment surfaces and the spin nut 330 and hexagonal collar 370a can inhibit longitudinal motion.

Figure 23:
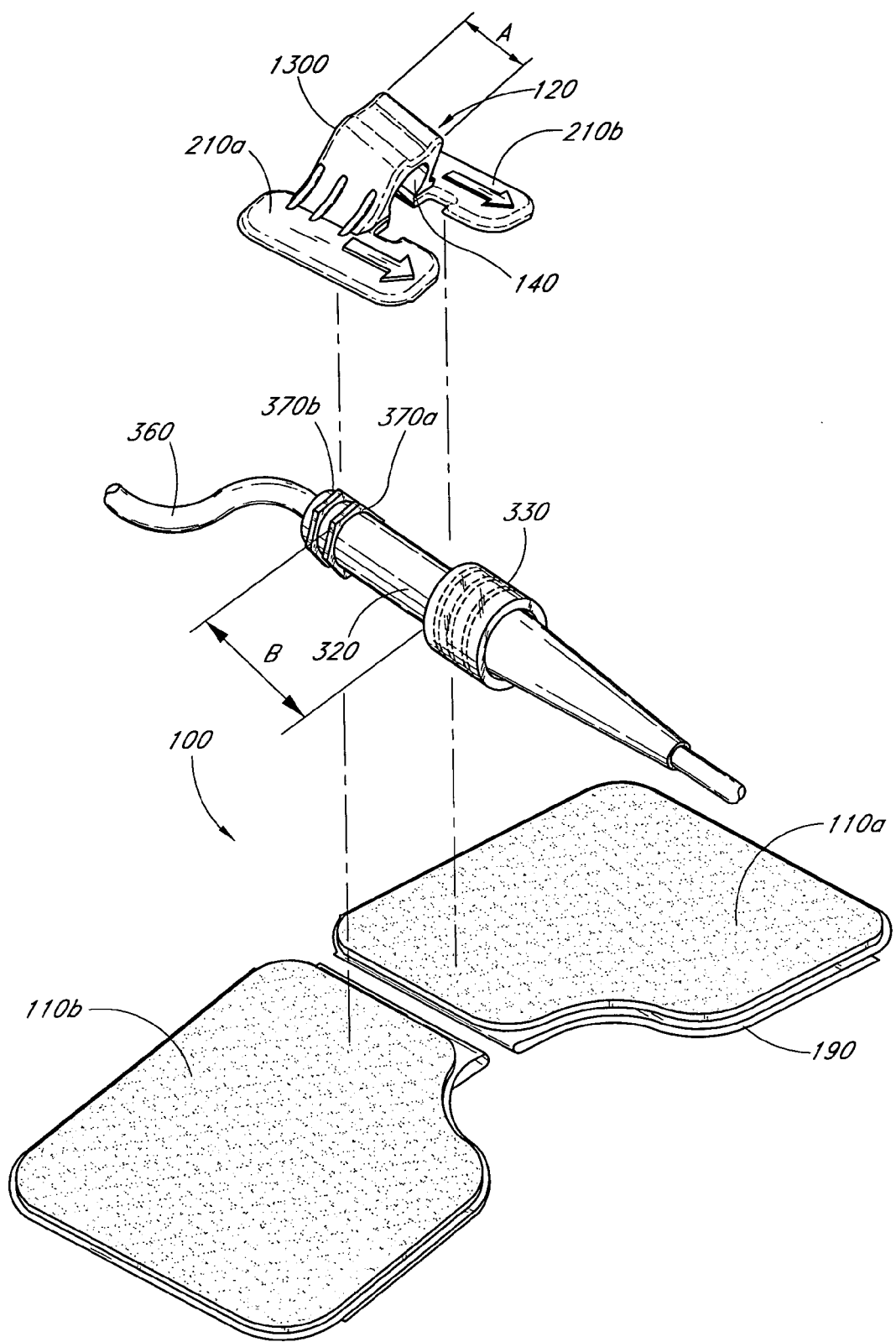
FIG. 23 is an exploded, perspective view of the connector fitting and the catheter hub of FIG. 15B, the elongated body of the connector fitting being aligned with the anchor pad and the retainer of FIG. 19.

In contrast to the connector fitting embodiments illustrated in FIGS. 20 and 21, the connector fitting illustrated in FIG. 15B does not include a radially extending member that is located between the ends of the connector fitting 300. The channel 140 of the retainer embodied in FIG. 19 forms an improved fit with the connector fitting illustrated in FIG. 15B as shown in FIG. 23. In FIG. 23, the retainer can generally abut against the spin nut and the hexagonal collar 370a to inhibit longitudinal movement.

Figure 24:
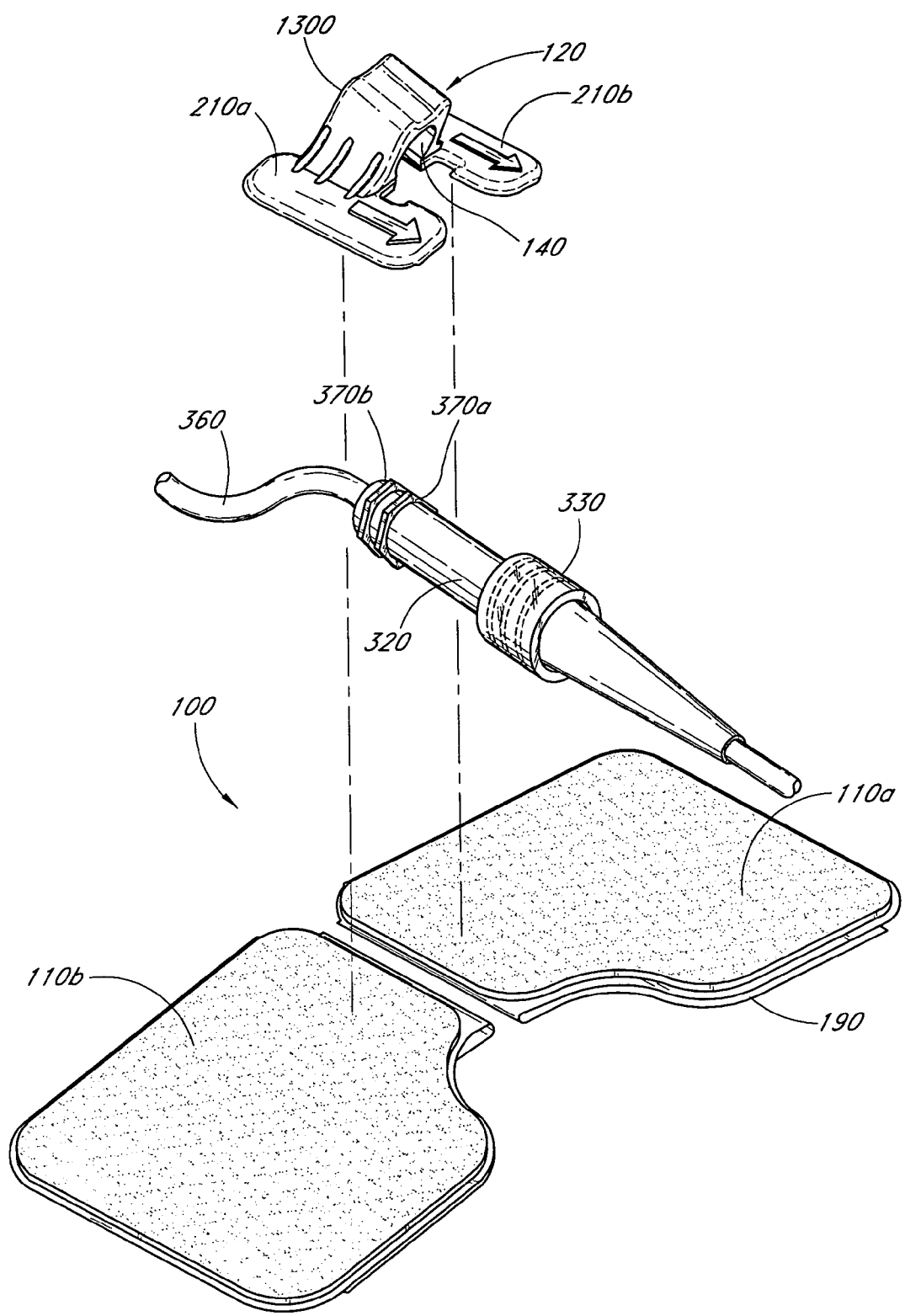
FIG. 24 is an exploded, perspective view of the connector fitting and the catheter hub of FIG. 15B, the collars of the connector fitting being aligned with the anchor pad and the retainer of FIG. 19.

Another embodiment illustrates the retainer 120 being pressed over radially extending members 370a, 370b (FIG. 24). Unlike the embodiments described with reference to FIGS. 22 and 23, the length of the retainer in FIG. 24 is not selected to fit between distal and proximal contact surfaces on the connector fitting. Instead, the body member 1300 in this embodiment includes one or more grooves, slots or other receptacles in the channel 140 for receiving the radially extending members 370a, 370b. The grooves or slots form abutment surfaces that abut against contact surfaces on the radially extending members 370a, 370b to inhibit longitudinal motion of the medical article.

Figure 25:
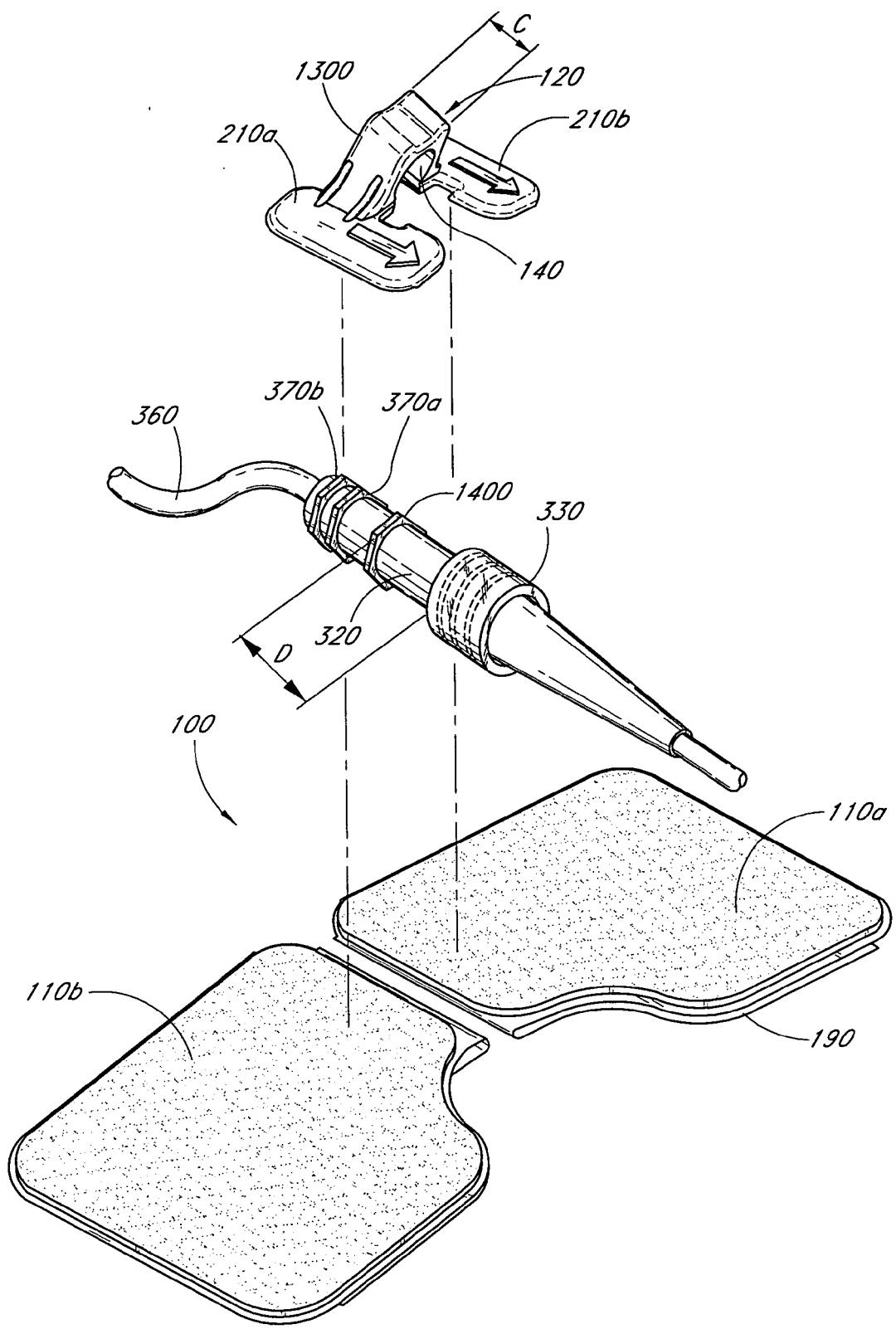
FIG. 25 is an exploded, perspective view of the connector fitting and the catheter hub of FIG. 20, a portion of the elongated body of the connector fitting being aligned with the anchor pad and the retainer of FIG. 19.

Another embodiment illustrates a retainer 120 designed to fit between the spin nut 330 and the hexagonal nut 1400 on the connector fitting (FIG. 20) as shown in FIG. 25. Unlike the embodiment illustrated in FIG. 22 where a groove or slot in the channel 140 provides a flush fit between the connector body 320 and the retainer, the retainer in FIG. 25 forms a flush fit without a groove or slot. Instead, the shorter length of the retainer in FIG. 25 allows the retainer to fit between two adjacent contact points or surfaces. For example, the retainer illustrated in FIG. 25 fits between the spin nut 330 and the hexagonal nut 1400.

An additional embodiment of a retainer is illustrated in FIGS. 27A–J and 28. Only the central channel 1500 of this embodiment differs from the above-described embodiment in that the central channel preferably has a generally constant cross-sectional shape (e.g., a generally constant diameter to cooperate with a tubular connector fitting body). In contrast to the retainer designs describe with reference to FIGS. 22 and 26, the constant cross-sectional shape of the retainer design described with reference to FIGS. 27A–J can form an improved fit with the constant diameter of the connector body 320.

A retainer in accordance with another embodiment of the invention is illustrated in FIG. 19, with FIG. 19 showing a perspective view of a retainer and anchor pads that are similar to FIG. 1 above. Only the body member 1300 of this embodiment differs from the above-described embodiment. Accordingly, the above description applies equally to the embodiment of FIG. 19, unless otherwise indicated.

The body member 1300 of the retainer 120 illustrated in FIG. 19 preferably is configured to retain a portion of a medical article that has a generally constant outer radius along its length. (In contrast, the embodiment of the retainer described with reference to FIGS. 1 and 16 was sized to retain a tapering portion of the medical article.) In the embodiment described with reference to FIG. 19, the inner surface of the inverted central channel 140 is sized to match or approximately match the outer radius of the medical article. To arrest longitudinal motion of the medical article, one or more abutment surfaces on the body member 1300 with one or more contacts on the medical article.

The inner surface of the central channel 140 in the illustrated embodiment has a generally semi-circular cross-sectional shape. The inner surface contour of the central channel 140 is selected depending on the diameter or geometry of the portion of the medical article to be retained. For example, since the retainer 120 in FIG. 19 is configured to retain a portion of a connector fitting that has a constant outer diameter (see, e.g., the connector fitting illustrated in FIG. 15A), the central channel can have a constant radius along its length. By matching the inner surface contour of the central channel 140 to the outer surface of the secured portion of the medical article, a more effective securement may be achieved.

Other embodiments of the retainer 120 can have an inner surface that is configured to match, or closely match, an outer surface of a raised portion of the connector fitting. Such a raised portion of the connector fitting can be in the form of two contact surfaces which together form a radially extending member, e.g., an annular collar, ring, or hex nut. By selecting an inside surface contour for the retainer that matches or closely matches the annular member, a form of snap-fit can be achieved between the retainer and the connector fitting when the connector fitting is engaged with the retainer.

The annular member and the connector fitting can be manufactured individually or as a unitary member. If the inside surface contour of the retainer 120 is substantially larger than the outer diameter of the connector fitting, an annular member can be installed around the connector fitting to allow a form of snap-fit between the outer diameter of the annular member and the inside surface of the retainer. In such an embodiment, the annular member alone may not inhibit longitudinal motion of the medical article. However, advantageously, the same retainer can be used with connector fittings with different outer diameters. Moreover, a connector fitting can include more than one annular member. Each annular member can have a different outer diameter whereby the connector fitting can be used with retainers 120 that have different inner surface diameters or the same diameter sufficiently sized to receive the irregularly shaped connector fitting. Additionally, in some forms of the retainer, abutments in the form of, for example, abutment surfaces that define, at least in part, a groove are employed to abut against one or both of the contact surfaces of the annular member. By engaging the groove with at least a portion of the annular member, longitudinal motion of the connector fitting relative to the retainer can be inhibited, as described below.

In addition or in the alternative, effective longitudinal securement between the retainer and the connector fitting can also be achieved by the engagement of the radially extending member or annular member between the retainer and the medical article. The radially extending member can be in the form of, for example, an annular collar as previously described. For example, a tab similar to the push tab on the catheter hub of FIG. 15A could be located on the outer surface of the connector fitting. The push tab could engage an abutment surface(s) in the form of a recess or receptacle on the inner surface of the retainer 120. The recess or receptacle in the retainer 120 can be in the form of, for example, a slot or groove. By engaging the push tab within the recess, longitudinal movement of the connector fitting with respect to the retainer is further limited. Exemplary radially extending members which can form a snap-fit with the inner surface of the retainer and/or engage a recess or groove in the retainer are described below with reference to FIGS. 21 and 22.

In addition or in the alternative, the longitudinal length of the retainer 120 can be selected to match, or closely match, the longitudinal distance between a first contact surface and a second contact surface of the connector fitting 320. The first and second contact surfaces can be in the form of first and second radially extending members that extend from the medical article. For example, the second radially extending member could be a spin nut of a catheter hub. For ease of discussion, the longitudinal length of the retainer 120 is illustrated in FIG. 19 as dimension A.

Connector fittings for use with the embodiment of the retainer illustrated in FIG. 19 are illustrated in FIGS. 20 and 21, with FIG. 20 showing a connector fitting and a catheter hub with a ring secured to the connector fitting, and FIG. 21 illustrating another connector fitting secured to a catheter hub with a radially extending tab secured to the connector fitting are similar to FIG. 15B above. Only the connector fitting of these embodiments differs from the above-described embodiment. Accordingly, the above description applies equally to the embodiments of FIG. 20–21, unless otherwise indicated.

FIG. 20 is a perspective view of a connector fitting secured to a catheter hub 430, with the connector fitting having two contact surfaces forming a ring 1400. The ring 1400 increases the diameter of the connector fitting to more closely match the inner surface of the retainer. By increasing the diameter of the connector fitting, the ring 1400 and the retainer can form a snap-fit. To arrest longitudinal movement of the medical article, the connector fitting can include contact surfaces in the form of a radially extending member 370*a* and spun nut 330. The ring 1400 is located between the radially extending member 370*a* and the spin nut 330. The contact surface on the proximal side of the radially extending member 370*a* can abut against an abutment surface in the form of a distal end of the retainer. Additionally, the contact surface on the distal side of the spin nut 330 can abut against an abutment surface in the form of a proximal end of the retainer. When the connector fitting is inserted into the adapter 430, the lumen of the connector fitting is disposed in fluid communication with the lumen of the adapter 430. This provides fluid communication between the medical line 360 and the patient.

The ring 1400 is illustrated as a hex nut located around the circumference of the elongated body 320 of the connector fitting 300. Alternatively, the ring 1400 can have a circular outer surface similar to the illustrated outside diameter of the spin nut 330. A non-circular shape may be preferred to further inhibit rotational movement of the retainer 120 around the longitudinal axis when the retainer is installed over the connector fitting. The ring 1400 need not have the same shape as the first or second radially extending members 370*a*, 370*b*. For instance, the ring 1400 can have a circular shape and the first and second radially extending members 370*a*, 370*b* can have the hexagonal shape illustrated.

The ring 1400 can be fixed to the elongated body 320 or allowed to slide in a longitudinal direction along the elongated body 320. Those of skill in the art will recognize that the ring 1400 need not have any particular shape or longitudinal thickness. In some applications, as described below in connection with FIG. 22, it may be preferable to increase the longitudinal length of the ring 1400 (i.e., make the ring thicker) to inhibit the ring from acting as a fulcrum when the connector fitting is inserted into the retainer illustrated in FIG. 22.

Alternatively, or in addition to the abutment surfaces described above, including one or more abutment surfaces in the inner surface of the retainer 120 can further inhibit longitudinal movement. Depending on the radial dimension of the ring 1400, the abutment surface(s) can extend into or through the wall of the retainer to form a groove or slot, respectively. The groove or slot receives at least a portion of the ring 1400. The groove or slot can be sized to either receive the ring in a loose or close-fit manner. With the addition of a groove, longitudinal movement of the connector fitting 300 relative to the retainer 120 can still be inhibited by the interaction between the ring 1400 and the groove within the central channel 140, especially if the ring 1400 fits closely into the groove.

Additionally or in the alternative to the one or more abutment surfaces or to the snap-fit engagement, at least a portion of the central channel 140 in all of the illustrated embodiments can be at least partially coated with an adhesive (e.g., an adhesive that preferably releasably holds the fitting within the retainer channel) to limit or restrict longitudinal movement. Alternatively, the medical article can include an adhesive section to hold the medical article in the channel and/or relative to the retainer.

The central channel 140 described with reference to FIG. 19 is configured to retain the outer surface of the ring 1400. In this way, the retainer 120 can snap-fit over the ring 1400, thereby retaining the medical article within the retainer. The central channel 140 can have a hexagonal or other non-circular shape to further inhibit rotational movement of the connector fitting with respect to the retainer 120.

As illustrated in FIG. 20, the longitudinal length between the spin nut 330 and the first radially extending member 370a is dimension B. With reference to FIGS. 19 and 20, the longitudinal length of the retainer 120, dimension A, can be selected to allow the retainer 120 to fit snugly between and preferably abut the contact surfaces of the first radially extending member 370a and the spin nut 330. As noted above, a slight gap can exist between the abutment and contact surfaces; however, a tighter fit will lessen any relative longitudinal movement between the retainer and the connector fitting. In this way, the connector fitting 300 will be inhibited from moving in a longitudinal direction relative to the retainer 120 once the connector fitting 300 is secured within the retainer.

Alternatively, the longitudinal length of the retainer 120, dimension A, is selected to be less than the distance between the first radially extending member 370a and the spin nut 330, dimension B. With dimension A less than dimension B, the ease by which the connector fitting is installed into the retainer 120 may be increased.

FIG. 21 is a perspective view of a connector fitting 300 secured to a catheter hub 430, with the connector fitting having two contact surfaces forming a tab 310. As briefly described with reference to FIG. 20, the tab 310 or ring 1400 can cooperate with a groove or slot 220 in the retainer to limit longitudinal movement of the medical article when installed in the retainer. In particular, it can be desirable for the longitudinal length of each slot 220 to be sufficient to receive the tab 310 of the medical article. The slot 220 receives the tab 310 from the retained portion of the medical article.

Combinations of the retainer 1300 with the connector fittings illustrated in FIGS. 15, 20, and 21 are illustrated in FIGS. 22–25. FIG. 22 is an exploded, perspective view of the connector fitting 300 and the catheter hub 430 of FIG. 20 with the ring 1400 of the connector fitting being aligned with the anchor pad and the retainer of FIG. 19. The inverted channel 140 in the retainer 120 is pressed over the connector fitting 300 whereby the connector fitting slides into the central channel of the body member 1300. The body member 1300 in this embodiment does not include grooves, slots or other receptacles for receiving the ring 1400. Rather, depending on the outer diameter of the ring 1400, a snap-fit between the ring 1400 and the inner surface of the body member 1300 can be formed. In addition, the longitudinal length of the ring 1400 (i.e., its thickness) can be selected to inhibit the ring from acting as a fulcrum point for the retainer 120. Alternatively, or in addition to, the longitudinal length of the body member 1300, dimension A, can be selected to fit between the first radially extending member 370a and the spin nut 330, dimension B. As previously described, the spin nut 330 and/or the first radially extending member 370a can arrest axial movement in one or two directions of the connector fitting 300 when installed in the retainer 120.

FIG. 23 is an exploded, perspective view of the connector fitting 300 and catheter hub 430 of FIG. 15B with the elongated body 320 of the connector fitting 300 being aligned with the anchor pad and the retainer of FIG. 19. The inverted channel 140 in the retainer 120 is pressed over the connector fitting 300 whereby the connector fitting slides into the central channel of the body member 1300. In the embodiment described with reference to FIG. 23, the channel 140 receives the elongated body 320 of the connector fitting 300 and is generally configured to house, to preferably grip, and to secure the elongated body 320. The elongated body may have a constant outer diameter. In the embodiment illustrated in FIG. 23, the channel 140 is configured to retain an elongated body 320 which has a constant outer diameter.

Alternatively the elongated body may incorporate one or more contact surfaces in the form of a varying outer diameter or a tapering outer surface. To engage with the tapering outer surface, the channel 140 can include one or more abutment surfaces in form of a matching tapering inner surface along its length. Additional embodiments of the central channel 140 of the retainer can comprise a plurality of different abutment surfaces in the form of radii and/or tapering regions. In this way, the size (i.e., radii, tapered) of the central channel 140 can be chosen to match or approximate the size of various standard connector fittings, catheter hubs or possibly all or portions of both. By matching the inner surface contour of the central channel 140 to the outer surface of the connector fitting, a more effective securement may be achieved.

In addition, if the longitudinal length of the retainer 120, shown as dimension A, is selected so that the retainer closely fits between the first radially extending member 370a and the spin nut 330, dimension B; the spin nut and the radially extending member will further inhibit axial motion in one or more directions through the central channel 140 of the retainer. Alternatively, if the longitudinal length of the retainer 120 is selected to be less than dimension B, the spin nut or the radially extending member will inhibit axial motion in one direction through the central channel 140. Additionally, the central channel can include an adhesive coating that covers at least a portion of the channel to hold the elongated body of the connector fitting relative to the retainer.

FIG. 24 is an exploded, perspective view of the connector fitting 300 and catheter hub 430 of FIG. 15B with the radially extending elements 370a, 370b of the connector fitting being aligned with an anchor pad and a body member 1300 of the retainer 120. The anchor pad and the retainer 120 of this embodiment are configured similar to the anchor pad and the retainer illustrated in FIG. 19; however, the size of the central channel differs in each embodiment. In the embodiment illustrated in FIG. 23, the lower channel in the retainer 120 is pressed over the radially extending members 370*a*, 370*b* whereby the connector fitting 300 slides into the central channel of the body member 1300. In contrast to the method of securing the connector fitting 300 to the retainer 120 in FIG. 23, the radially extending members 370*a*, 370*b* shown in FIG. 24 fit within the central channel 140 of the body member 1300. The connector fitting 300 preferably includes one or more contact surfaces in the form of radially extending members 370*a*, 370*b* as shown in the illustrated embodiment. The radially extending members 370*a*, 370*b* can provide a snap-fit between the connector fitting 300 and the body member 1300. That is, the size and shape of the channel closely matches that of the radially extending members 370*a*, 370*b*. However, the engagement between the connector fitting and the retainer 120 may not arrest longitudinal movement of the medical article.

Additionally, one or more abutment surfaces in the inner surface of the retainer 120 can further inhibit longitudinal movement. Depending on the radial dimensions of the radially extending members 370*a*, 370*b*, the abutment surface(s) can extend into or through the wall of the retainer to form a groove or slot, respectively. The groove or slot receives at least a portion of the radially extending members 370*a*, 370*b*. The groove or slot can be sized to either receive the radially extending members 370*a*, 370*b* in a loose or close-fit manner. With the addition of a groove, longitudinal movement of the connector fitting 300 relative to the retainer 120 can still be inhibited by the interaction between the radially extending members 370*a*, 370*b* and the groove within the central channel 140, especially if the radially extending members 370*a*, 370*b* fits closely into the groove.

Additionally or in the alternative, at least a portion of the central channel 140 can be coated with an adhesive (e.g., an adhesive that releasably holds the fitting within the retainer channel).

FIG. 25 is an exploded, perspective view of the connector fitting 300 and the catheter hub 430 of FIG. 20 with a portion of the elongated body of the connector fitting being aligned with the anchor pad and the retainer of FIG. 19. The central channel 140 in the retainer 120 is pressed over the connector fitting whereby the connector fitting slides between the anchor pads 110(*a*), 110(*b*) and into the central channel 140 of the body member 1300. As illustrated in FIG. 25, the longitudinal length of the body member 1300, denoted as dimension C, is selected to fit between the spin nut 330 and the ring 1400, dimension D. The longitudinal length of the body member 1300 can be selected to closely fit between the contact surface of the ring 1400 and the contact surface of the spin nut 330. In such a configuration, axial movement of the connector fitting 300 with respect to the retainer 120 can be inhibited by engagement between the abutment surfaces of the retainer and the contact surfaces of the connector fitting. Alternatively, the dimension C is selected to fit between the first radially extending member 370*a* and the ring 1400.

Additional embodiments of the central channel 140 of the retainer can comprise a plurality of different abutment surfaces in the form of radii and/or tapering regions. In this way, the size (i.e., radii, tapered) of the central channel 140 can be chosen to match or approximate the size of various standard connector fittings. By matching the inner surface contour of the central channel 140 to the outer surface of the connector fitting, a more effective securement may be achieved.

FIG. 26 is an exploded, perspective view of the connector fitting 300 and catheter hub 430 of FIG. 20 with the connector fitting being aligned with the anchor pad and the retainer of FIG. 1. As shown, the connector fitting 300 includes two contact surfaces in the form of a ring 1400 which fits between two of the abutment surfaces that form one of the lateral slots 220 in the retainer. In this way, the ring 1400 will fit within one of the slots 220, thereby arresting longitudinal movement of the connector fitting 300 when installed in the retainer 120. The slots 220 have a longitudinal length sufficient to accept the ring 1400 of the retained medical article.

The inverted central channel 140 in the retainer 120 is pressed over the connector fitting 300 whereby the connector fitting slides between the anchor pads 110(*a*), 110(*b*) and into the central channel of the body member 130. When guided through the lower opening 150 by the healthcare provider, the elongated body of the connector fitting 300 will lie within the central channel 140 of the retainer 120. Depending on the diameter of the ring 1400 and the outer diameter of the connector fitting, a snap-fit between the ring and the body member 130 can be formed. The abutment surfaces forming the slots 220 will inhibit longitudinal migration of the connector fitting 300 through the central channel 140 of the retainer 120.

In addition, if the longitudinal length of the retainer 120, shown as dimension A, is selected so that the retainer can fit between the contact surface of the first radially extending member 370*a* and the contact surface of the spin nut 330, dimension B, the spin nut and the radially extending member will further inhibit axial motion in one or more directions through the central channel 140 of the retainer. Alternatively, if the longitudinal length of the retainer 120 is selected to be less than dimension B, the spin nut or the radially extending member will inhibit axial motion in one direction through the central channel 140. Such a technique may be an effective form of additional securement in some applications.

The combination of the channel shape (constant radius), the entering engagement between the abutment surfaces and the ring 1400 on the connector fitting, and the longitudinal length of the body member 130 of the retainer 120 arrest movement of the retained section of the medical article in three dimensions: longitudinally, laterally, and transversely. Further, the wall 290 prohibits the connector fitting from 360-degree rotation while the connector fitting is installed in the retainer.

A retainer in accordance with another embodiment of the invention is illustrated in FIGS. 27A through 27J that are similar to the retainer described in FIGS. 1–13 and 26 above. Only the central channel 1500 of this embodiment differs from the above-described embodiment in that the central channel preferably has a generally constant cross-sectional shape (e.g., a generally constant diameter to cooperate with a tubular connector fitting body). Accordingly, the above description applies equally to the embodiment of FIGS. 27A through 27J, unless otherwise indicated.

Figure 27A:
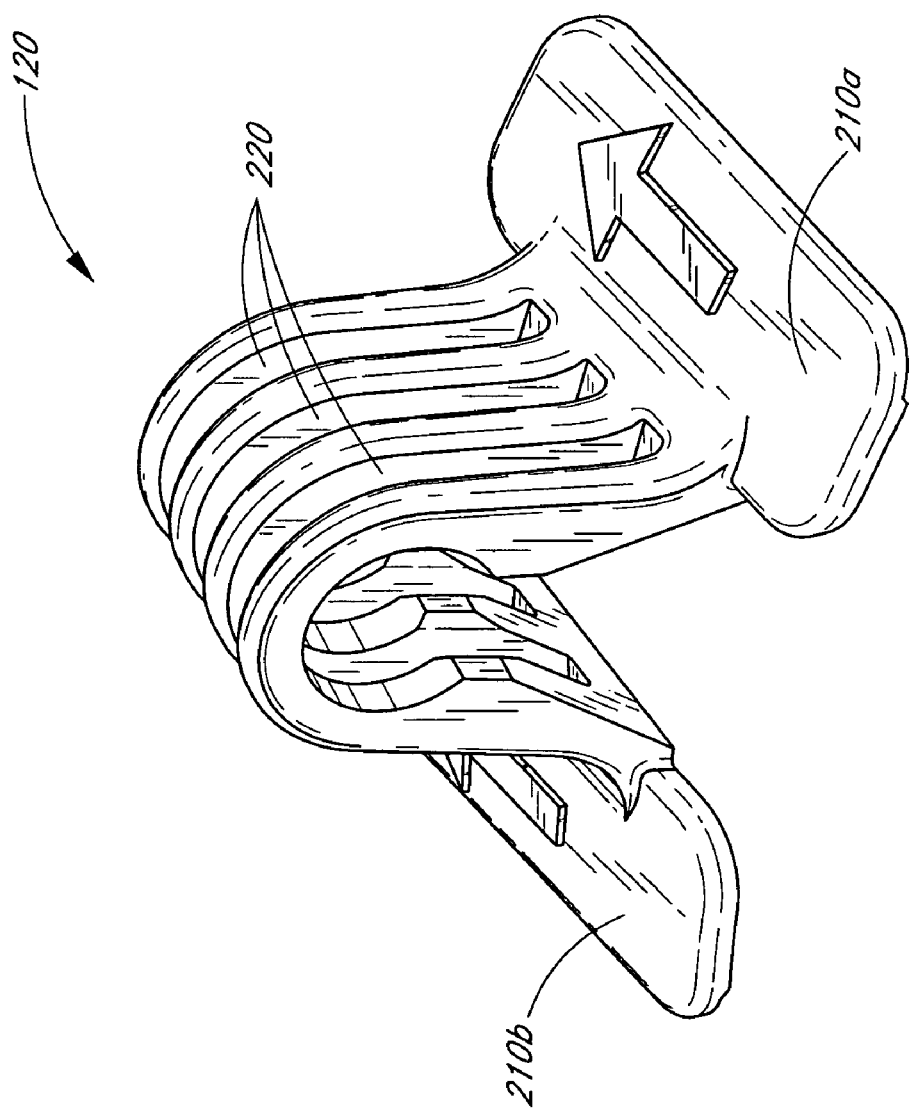
FIG. 27A is a rear perspective view of a retainer configured in accordance with another preferred embodiment of the present invention.
Figure 27C:
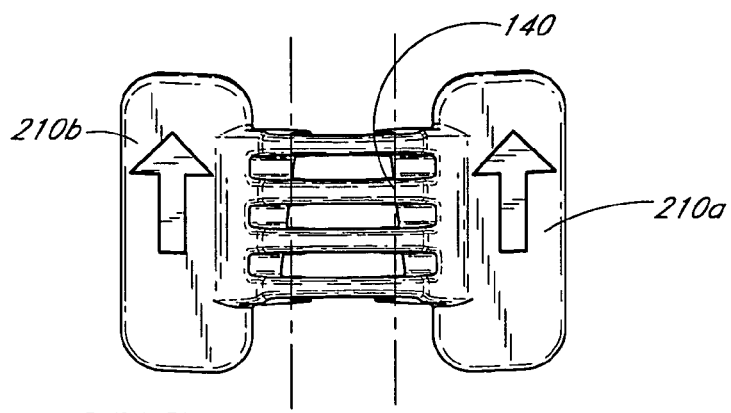
FIG. 27C is a top plan view of the retainer of FIG. 27A.
Figure 27D:
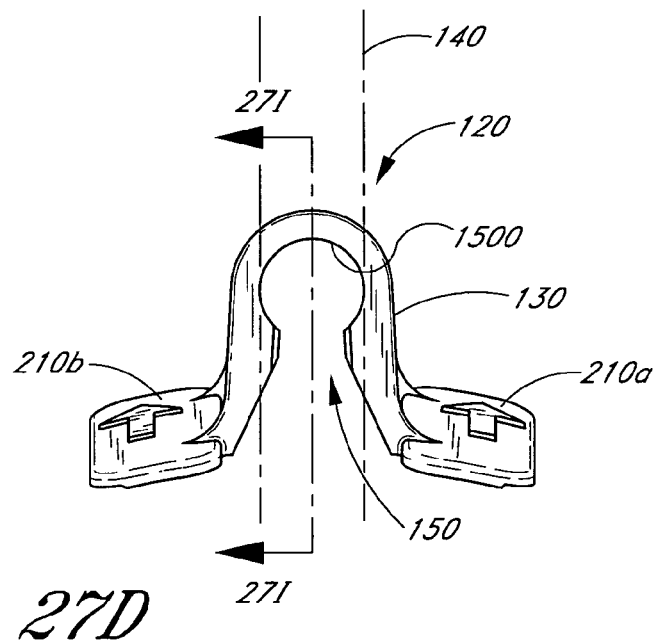
FIG. 27D is a rear elevational view of the retainer of FIG. 27C.
Figure 27E:
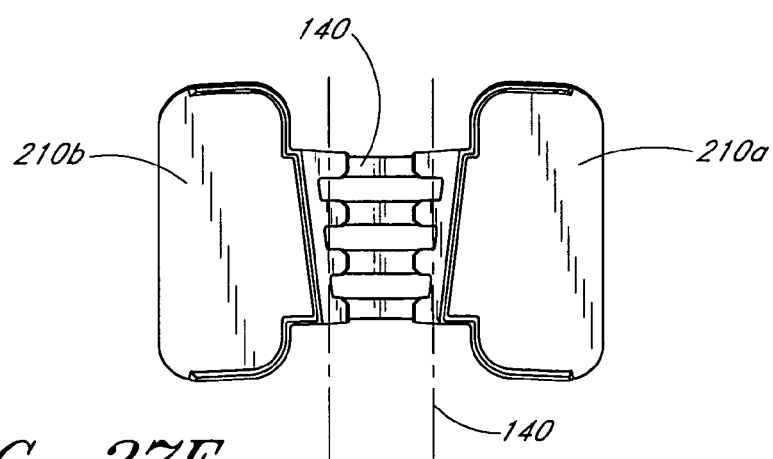
FIG. 27E is a bottom plan view of the retainer of FIG. 27D.
Figure 27F:
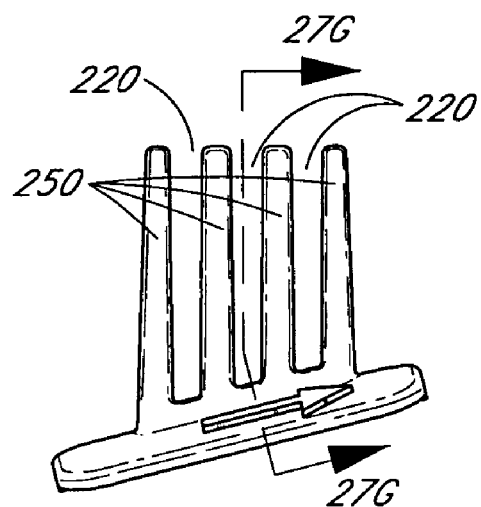
FIG. 27F is a side elevational view of the retainer of FIG. 27A.
Figure 27G:
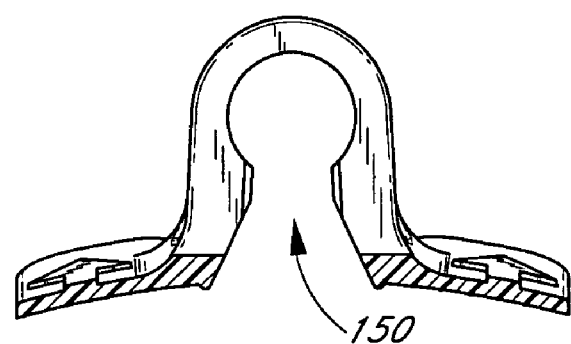
FIG. 27G is a cross-sectional view of the retainer of FIG. 27F taken along line 27G—27G.
Figure 27H:
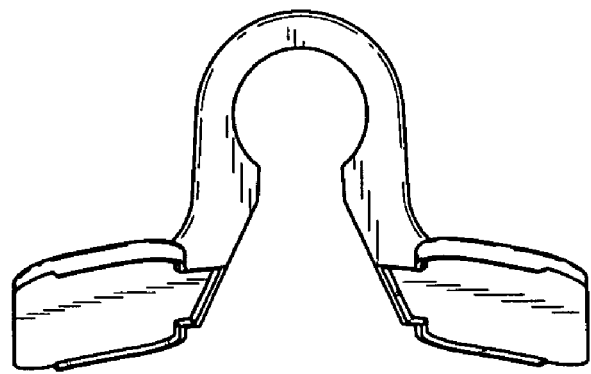
FIG. 27H is a front view of the retainer of FIG. 27C.
Figure 27I:
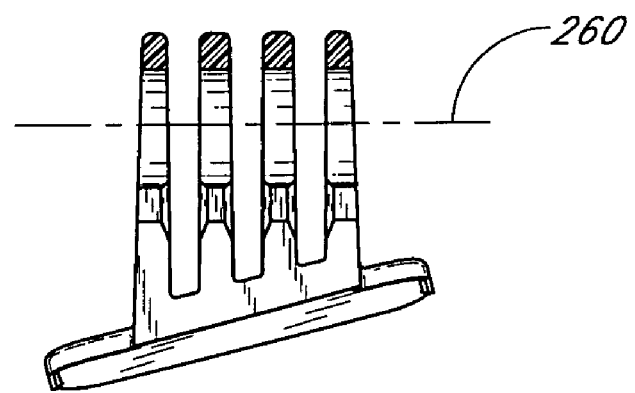
FIG. 27I is a cross-sectional view of the retainer of FIG. 27D taken along line 27I—27I.

The retainer 120 illustrated in FIGS. 27A–27J includes a body 130 that defines a central channel 1500 and a pair of mounting feet 210*a*, 210*b* disposed on opposite sides of the body 130. The opening into the central channel 1500 is chamfered to ease insertion of the fitting connector into the retainer 120. The bottoms of the mounting feet 210*a*, 210*b* generally define a plane and a central axis of the central channel 1500 that is skewed relative to the plane, as best seen in FIGS. 27F and 27I.

The body 130 preferably defines at least two abutment surfaces to form one slot 220 and more preferably defines additional abutment surfaces to form additional slots 220. The slots 220 are sized to one or more contact surfaces on the connector fitting. For example, as illustrated in the present embodiment shown in FIG. 27J and 28, each slot can receive contact surfaces in the form of the hex nut rings 370a, 370b, 1400, and/or connector tabs 310 that are included on the various connector fittings illustrated in FIGS. 15A, 15B, 20, and 21.

Figure 27J:
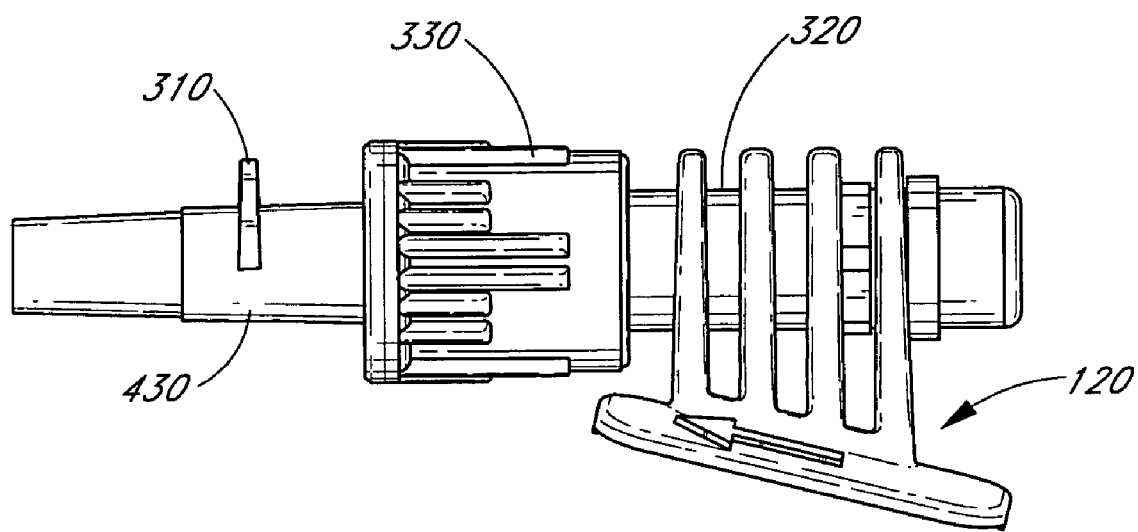
FIG. 27J is a side elevational view of the retainer of FIG. 27F engage with a connector fitting that is secured to a catheter hub.
Figure 28:
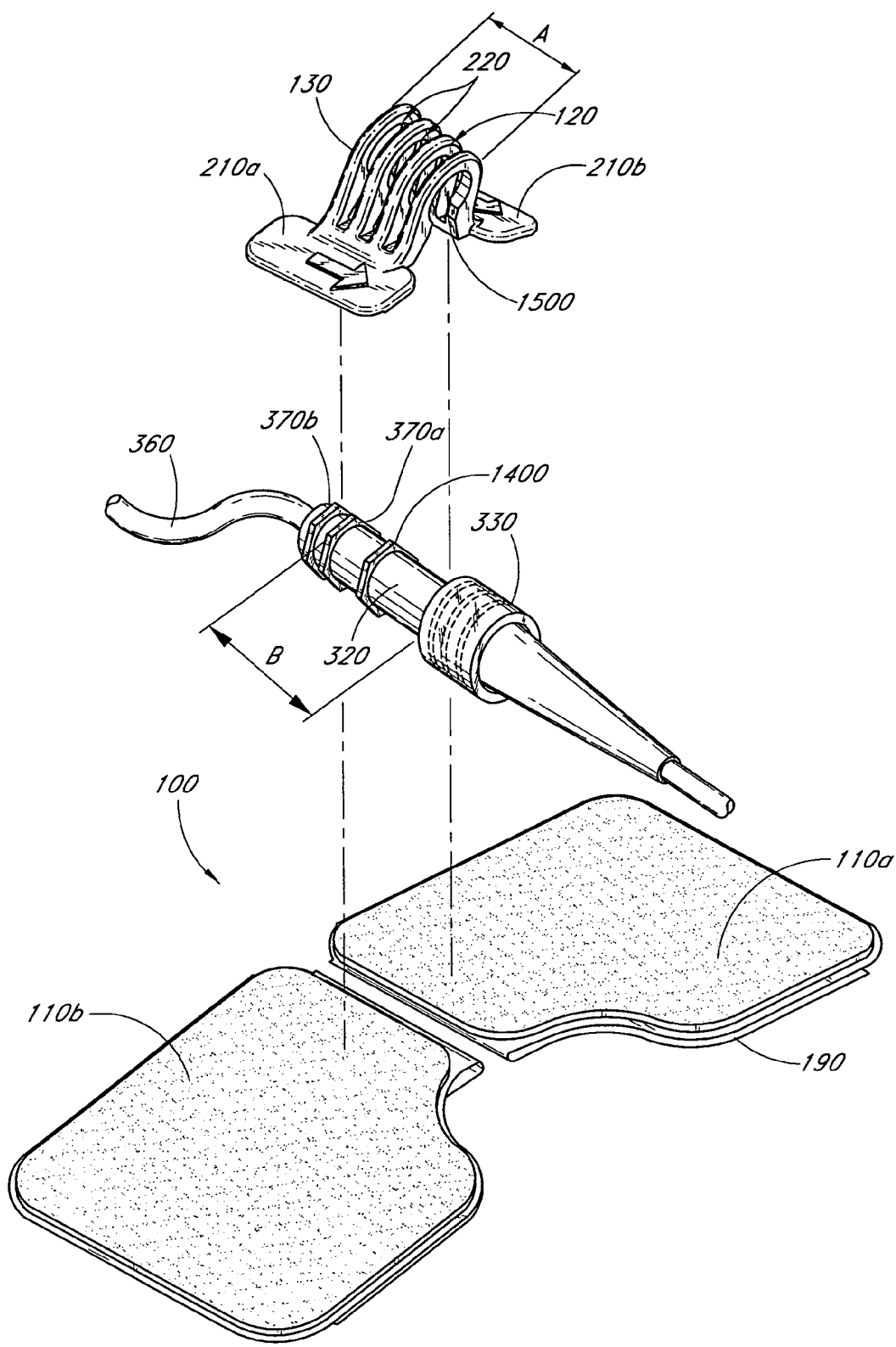
FIG. 28 is an exploded, perspective view of the connector fitting and the catheter hub of FIG. 20, the connector fitting being aligned with an anchor pad and a retainer of the securement device of FIG. 27A.

The longitudinal length of the body 130 preferably is sized so that abutment surfaces located at the proximal and distal ends of the retainer fit closely between the distal contact surface of the spin nut 330 and the proximal contact surface of the hex nut ring 370a when the spin nut is engages with a catheter hub, as illustrated in FIG. 15B. In this manner, the retainer body 130 lies between the contact surface of the spin nut 330 and the contact surface of the hex nut ring 370a to inhibit longitudinal movement of the connector fitting (and the attached catheter hub) relative to the retainer, which is adapted to be secured to the patient. If, however, the healthcare provider positions the retainer 120 on the connector fitting at a position farther from the spin nut 330, as seen in FIG. 27J, the retainer can still receive the connector fitting body, as well as one or both of the hex nut rings. The interaction between the abutment surfaces of the retainer and the contact surfaces of the hex nut ring(s) generally arrests longitudinal movement. In addition or in the alternative to such interaction between the retainer and the hex nut ring(s), the retainer can also include an adhesive coating that covers at least a portion of the central channel 1500. The adhesive coating in one preferred form releasably holds the connector fitting to the retainer to inhibit movement of the connector fitting relative to the fitting. Such adhesive, in other variations of the retainer, can more permanently attach the connector fitting to the retainer.

The various embodiments of securement devices and techniques described above thus provide a number of ways to provide safe and releasable securement for medical articles to the skin of a patient. In addition, the techniques described may be broadly applied for use with a variety of medical lines and medical procedures.

Of course, it is to be understood that not necessarily all such objectives or advantages may be achieved in accordance with any particular embodiment using the systems described herein. Thus, for example, those skilled in the art will recognize that the systems may be developed in a manner that achieves or optimizes one advantage or group of advantages as taught herein without necessarily achieving other objectives or advantages as may be taught or suggested herein.

Furthermore, the skilled artisan will recognize the interchangeability of various features from different embodiments. Although these techniques and systems have been disclosed in the context of certain embodiments and examples, it will be understood by those skilled in the art that these techniques and systems may be extended beyond the specifically disclosed embodiments to other embodiments and/or uses and obvious modifications and equivalents thereof. Additionally, it is contemplated that various aspects and features of the invention described can be practiced separately, combined together, or substituted for one another, and that a variety of combination and subcombinations of the features and aspects can be made and still fall within the scope of the invention. Thus, it is intended that the scope of the systems disclosed herein disclosed should not be limited by the particular disclosed embodiments described above.

What is claimed is:

1. A retainer configured for use with a medical article, the retainer comprising:
 a body member comprising,
  a channel formed through the body member and having a central axis, the channel being configured to retain at least a portion of the medical article within the body member with the retained portion extending entirely through the channel, the channel having a longitudinal access opening disposed on an underside of the body member to allow at least ingress of at least the retained portion of the medical article into the channel,
  at least one abutment extending generally normal to the central axis of the channel and configured to inhibit longitudinal movement of the medical article relative to the retainer, and
  at least one support having a lower surface disposed on the underside of the retainer and to a side of the access opening opposite the channel axis, the lower surface being located below the channel and at a distance spaced from the central axis, the distance being greater than a distance between a lower extremity of the retained portion of the medical article and the central axis so as to inhibit contact between at least the lower extremity of the retained portion of the medical article and a patient's skin when the retainer is placed upon the patient's skin.

2. A retainer as in claim 1 wherein the at least one abutment is configured to abut against a contact surface on the medical article to arrest movement of the medical article in at least one direction.

3. A retainer as in claim 2 wherein the abutment has a generally complimentary shape to at least a portion of a radially extending member of the medical article.

4. A retainer as in claim 3, wherein the retainer comprises two abutments arranged to form a slot therebetween, and the slot is configured to receive the radially extending member when the medical article is inserted into the channel.

5. A retainer as in claim 4, further comprising a stop member which extends into a portion of the slot such that when the medical article is inserted into the channel and rotated in a first direction around the axis of the channel, the radially extending member slides within the slot until the radially extending member contacts the stop member.

6. A retainer as in claim 3, wherein the radially extending member extends about the circumference of the medical article.

7. A retainer as in claim 3, wherein the radially extending member extends substantially parallel to the medical article.

8. A retainer as in claim 1, wherein the channel has a tapering shape.

9. A retainer as in claim 8, wherein the tapering shape of the channel generally matches a tapering shape of the retained portion of the medical article.

10. A retainer as in claim 9, wherein the tapering shape of the channel is selected to match substantially the tapering shape of the medical article to inhibit longitudinal movement of the retained portion of the medical article in a first direction when the retained portion of the medical article is inserted into the channel.

11. A retainer as in claim 10, wherein the at least one abutment is configured to abut against a contact surface on the retained portion of the medical article to limit longitudinal movement of the medical article in a second direction.

12. A retainer as in claim 1, wherein the retainer comprises a retention surface which is configured to inhibit transverse motion of the medical article.

13. A retainer as in claim 12, wherein the retention surface is located in the channel.

14. A retainer as in claim 12, wherein the retention surface provides a snap-fit securement with the portion of the medical article.

15. A retainer as in claim 12, wherein the retention surface flexes when the medical article is inserted into the channel.

16. A retainer as in claim 15, wherein the retention surface is a movable wall.

17. A retainer as in claim 12, wherein the channel has a radius of R and wherein the retention surface is located at a distance of greater than R from the axis of the channel.

18. A retainer as in claim 1, wherein the at least one support is a mounting wing coupled to the body member.

19. A retainer as in claim 1, wherein the at least one abutment is located between proximal and distal ends of the body member along the axis of the channel.

20. A retainer as in claim 1, wherein the at least one abutment is a surface on a proximal end of the body member.

21. A retainer as in claim 1, wherein the at least one abutment is located on a distal end of the body member.

22. A retainer as in claim 1, wherein the body member is configured to retain a medical article in the shape of a catheter hub.

23. A retainer as in claim 1, wherein the body member is configured to retain a medical article having two contact surfaces, and wherein the body member of the retainer is sized to fit between the two contact surfaces.

24. A retainer as in claim 1, wherein the body member comprises two abutments and is configured to retain a medical article having two contact surfaces.

25. A retainer as in claim 1, wherein at least a portion of the channel has an arc length of greater than 180 degrees.

26. A retainer as in claim 1, wherein the abutment comprises an adhesive, the adhesive adhering to the medical article when the medical article is inserted into the retainer.

27. A retainer as in claim 1, wherein a portion of the body member is transparent to facilitate alignment and ingress when inserting the medical article into the channel.

28. A retainer as in claim 1, wherein the abutment comprises a wall of a slot.

29. A retainer as in claim 1, wherein the abutment comprises a ridge.

30. A retainer as in claim 1, wherein the abutment comprises a protuberance.

31. A retainer configured for use with a medical article, the retainer comprising:
 a body member comprising,
  a channel formed through the body member and having a central axis, the channel being configured to retain at least a portion of the medical article within the body member with the retained portion extending entirely through the channel, the channel having a longitudinal access opening disposed on an underside of the body member to allow ingress of at least the retained portion of the medical article into the channel,
  at least one abutment extending generally normal to the central axis of the channel and configured to inhibit longitudinal movement of the medical article relative to the retainer, and
 means for inhibiting contact between a lower extremity of the retained portion of the medical article and a patient's skin.

32. A retainer configured for use with a medical article that comprises a radially extending member, the retainer comprising:
 a body member having proximal and distal ends and further comprising,
  a channel formed through the body member and having a central axis, the channel being configured to retain at least a portion of the medical article within the body member with the retained portion extending entirely through the channel, the channel having a longitudinal access opening disposed on an underside of the body member to allow at least ingress of at least the retained portion of the medical article into the channel, the channel being located within the body member so that a lower extremity of the retained medical article is spaced at a distance from the central axis, the distance being less than a distance between a lower extremity of the body member and the central axis so as to inhibit contact between the retained portion of the medical article and a patient's skin when the retainer is placed upon the patient's skin,
  at least one slot disposed between the proximal and distal ends of the body member and configured to receive the radially extending member, and
  a stop member extending into a portion of the at least one slot such that when the medical article is inserted into the channel and rotated in a first direction around the axis of the channel, the radially extending member slides within the slot until the radially extending member contacts the stop member.

33. A retainer as in claim 32, wherein the body member further comprises at least one support disposed on the underside of the retainer and to a side of the access opening opposite the channel axis.

34. A retainer as in claim 33, wherein the retainer comprises a retention surface which is configured to inhibit transverse motion of the medical article in at least one direction.

35. A retainer configured for use with a medical article, the retainer comprising:
 a body member comprising,
  a channel formed therethrough and having a central axis, the channel being configured to retain a portion of the medical article within the body member with the retained portion extending entirely through the channel, the channel having a longitudinal access opening disposed on an underside of the body member to allow ingress of at least the retained portion of the medical article into the channel,
  at least one abutment extending generally normal to the central axis of the channel and configured to inhibit longitudinal movement of the medical article relative to the retainer, and
  at least one support disposed on the underside of the retainer and to a side of the access opening opposite the channel axis, wherein a distance between the at least one support and the central axis of the channel is greater than a distance between a lower extremity of the retained portion of the medical article and the central axis so as to inhibit contact between at least the retained portion of the medical article and a patient's skin when the retainer is placed upon the patient's skin.

36. A retainer as claim 35, wherein the channel comprises at least two portions that are spaced apart with the at least one abutment disposed in between the portions of the channel, each portion extending about the central axis.

37. A retainer configured for use with a medical article, the retainer comprising:

a body member comprising, a channel formed therethrough and having a central axis, the channel being configured to retain at least a portion of the medical article within the body member with the retained portion extending entirely through the channel, the channel having a longitudinal access opening disposed on an underside of the body member to allow ingress of at least the retained portion of the medical article, at least one abutment extending generally normal to the central axis of the channel and configured to inhibit longitudinal movement of the medical article relative to the retainer, at least one support surface disposed on the underside of the retainer and to one side of the access opening opposite the channel axis, wherein the support surface is disposed below the channel and at a distance spaced from the central axis, which is greater than a distance between a lower extremity of the retained portion of the medical article and the central axis, so as to inhibit contact between the lower extremity of the retained portion of the medical article and the patient's skin when the retainer is placed upon the patient's skin, and wherein the support surface is angled relative to the central axis of the channel to define an incident angle between the central axis of the channel and the patient's skin.

* * * * *

UNITED STATES PATENT AND TRADEMARK OFFICE
CERTIFICATE OF CORRECTION

PATENT NO. : 7,014,627 B2
APPLICATION NO. : 10/642445
DATED : March 21, 2006
INVENTOR(S) : Steven F. Bierman It is certified that error appears in the above-identified patent and that said Letters Patent is hereby corrected as shown below:

On the Title Page, Item -56- (Other Publications), Line 3, after "U.S." insert -- design --.

In Column 3, Line 67, delete "Fig. 5;" and insert -- Fig. 5. --, therefore.

In Column 7, Line 40 (approx.), delete "comer" and insert -- corner --, therefore.

In Column 7, Line 63, delete "medical grade" and insert -- medical-grade --, therefore.

In Column 8, Line 43, delete "comer" and insert -- corner --; therefore.

In Column 9, Line 13, delete "10(b)." and insert -- 110(b). --, therefore.

In Column 11, Line 21, delete "snap fit" and insert -- snap-fit --, therefore.

In Column 16, Line 61, delete "an" and insert -- a --, therefore.

In Column 17, Line 33, delete "an" and insert -- a --, therefore.

In Column 19, Line 11 (approx.), delete "heathcare" and insert -- healthcare --, therefore.

In Column 20, Line 21, delete "heathcare" and insert -- healthcare --, therefore.

In Column 21, Line 1, delete "connector-fitting" and insert -- connector fitting --, therefore.

In Column 30, Line 35, in Claim 2, after "claim 1" insert -- , --.

UNITED STATES PATENT AND TRADEMARK OFFICE
CERTIFICATE OF CORRECTION

PATENT NO. : 7,014,627 B2
APPLICATION NO. : 10/642445
DATED : March 21, 2006
INVENTOR(S) : Steven F. Bierman It is certified that error appears in the above-identified patent and that said Letters Patent is hereby corrected as shown below:

In Column 30, Line 39, in Claim 3, after "claim 2" insert -- , --.

Signed and Sealed this

Fifth Day of June, 2007

JON W. DUDAS
*Director of the United States Patent and Trademark Office*